US010539487B2

(12) United States Patent
Taft et al.

(10) Patent No.: US 10,539,487 B2
(45) Date of Patent: *Jan. 21, 2020

(54) SYSTEMS AND METHODS FOR MONITORING TISSUE SAMPLE PROCESSING

(71) Applicant: Ventana Medical Systems, Inc., Tucson, AZ (US)

(72) Inventors: Jefferson Curtis Taft, Sahuarita, AZ (US); David Chafin, Tucson, AZ (US); Michael Otter, Tucson, AZ (US); Benjamin Stevens, Oro Valley, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/843,828

(22) Filed: Mar. 15, 2013

(65) Prior Publication Data

US 2013/0224791 A1   Aug. 29, 2013

Related U.S. Application Data

(63) Continuation-in-part of application No. 13/372,040, filed on Feb. 13, 2012, now Pat. No. 10,126,216, which is a continuation-in-part of application No. PCT/US2011/027284, filed on Mar. 4, 2011.

(60) Provisional application No. 61/464,479, filed on Mar. 4, 2011, provisional application No. 61/463,551, filed on Feb. 17, 2011, provisional application No. 61/310,653, filed on Mar. 4, 2010.

(51) Int. Cl.
  *G01N 1/30* (2006.01)
  *G01N 1/31* (2006.01)
  *G01N 29/07* (2006.01)
  *G01N 29/44* (2006.01)

(52) U.S. Cl.
  CPC ............... *G01N 1/30* (2013.01); *G01N 29/07* (2013.01); *G01N 29/4418* (2013.01); *G01N 1/31* (2013.01); *G01N 2291/02475* (2013.01); *G01N 2291/02491* (2013.01)

(58) Field of Classification Search
  CPC ................................ G01N 1/30; A61K 9/0051
  USPC ........................................ 435/40.52; 422/536
  See application file for complete search history.

(56) References Cited

U.S. PATENT DOCUMENTS

| 3,961,097 A | 6/1976 | Gravlee, Jr. |
| 4,275,149 A | 6/1981 | Litman et al. |
| 4,318,980 A | 3/1982 | Boguslaski et al. |
| 4,495,817 A | 1/1985 | Hunt et al. |
| 4,656,047 A | 4/1987 | Kok et al. |
| 4,839,194 A | 6/1989 | Malluche et al. |
| 4,891,239 A | 1/1990 | Dudley et al. |
| 5,089,288 A | 2/1992 | Berger |
| 5,197,475 A | 3/1993 | Antich et al. |
| 5,523,204 A | 6/1996 | Singer et al. |
| 5,595,707 A | 1/1997 | Copeland et al. |
| 5,639,423 A | 6/1997 | Northrup et al. |
| 5,654,200 A | 8/1997 | Copeland et al. |
| 5,665,141 A | 9/1997 | Vago |
| 5,983,723 A | 11/1999 | Buckin et al. |
| 5,984,881 A | 11/1999 | Ishibashi et al. |
| 6,004,762 A | 12/1999 | Tse et al. |
| 6,042,874 A | 3/2000 | Visinoni et al. |
| 6,207,408 B1 | 3/2001 | Essenfeld et al. |
| 6,291,180 B1 | 9/2001 | Chu |
| 6,296,809 B1 | 10/2001 | Richards et al. |
| 6,352,861 B1 | 3/2002 | Copeland et al. |
| 6,582,962 B1 | 6/2003 | Richards et al. |
| 6,586,713 B2 | 7/2003 | Essenfeld et al. |
| 6,746,848 B2 | 6/2004 | Smith |
| 6,793,890 B2 | 9/2004 | Morales et al. |
| 6,875,583 B2 | 4/2005 | Giberson et al. |
| 7,075,045 B2 | 7/2006 | Visinoni |
| 7,090,974 B2 | 8/2006 | Chu |
| 7,262,022 B2 | 8/2007 | Chu |
| 7,300,439 B2 | 11/2007 | May |
| 7,666,620 B2 | 2/2010 | Wiederhold |
| 7,687,255 B2 | 3/2010 | Chu |
| 7,767,434 B2 | 8/2010 | Chu |
| 2002/0177183 A1 | 11/2002 | Giberson et al. |
| 2003/0197008 A1 | 10/2003 | Giberson et al. |

(Continued)

FOREIGN PATENT DOCUMENTS

EP  0660930 B1  11/1999
EP  1410811 A1  4/2004

(Continued)

OTHER PUBLICATIONS

Hall et al. (IEEE Transactions on Ultrasonics, ferroelectrics, and frequency control, vol. 47, No. 4, p. 1051-1056, 2000).*
Oldenburg et al. (Physics in Medicine and Biology, vol. 55, No. 4, p. 1189-1201, 2010; published Feb. 2, 2010).*
Hokfelt et al. (Histochemie, vol. 29, p. 325-339, 1972).*
Srinivasan et al. (American Journal of Pathology, vol. 161, No. 6, p. 1961 1971, 2002).*
Baldwin et al., Measurements of the anisotropy of ultrasonic velocity in freshly excised and formalin-fixed myocardial tissue, J Acoust Soc Am. Jul. 2005 ; 118(1): 505-513.*
Gueuning et al., Accurate Distance Measurement by an Autonomous Ultrasonic System Combining Time-of-Flight and Phase-Shift Methods., IEEE Instrumentation and Measurement Technology Conference, Belgium, Jun. 4-6, 1996.*

(Continued)

Primary Examiner — Taeyoon Kim
Assistant Examiner — Srikanth Patury
(74) Attorney, Agent, or Firm — Charney IP Law LLC; Thomas Finetti

(57) ABSTRACT

A tissue sample that has been removed from a subject can be evaluated. A change in speed of the energy traveling through the sample is evaluated to monitor changes in the biological sample during processing. The monitoring can detect movement of fluid with the sample and cross-linking. A system for performing the method can include a transmitter that outputs the energy and a receiver configured to detect the transmitted energy.

18 Claims, 28 Drawing Sheets

(56) References Cited

U.S. PATENT DOCUMENTS

| | | |
|---|---|---|
| 2004/0029184 A1 | 2/2004 | Gourevitch |
| 2004/0267263 A1 | 12/2004 | May |
| 2005/0269315 A1 | 12/2005 | Visinoni et al. |
| 2007/0072258 A1 | 3/2007 | Chu |
| 2008/0102006 A1 | 5/2008 | Kram et al. |
| 2008/0108043 A1 | 5/2008 | Wiederhold |
| 2008/0188767 A1 | 8/2008 | Oaki et al. |
| 2008/0221449 A1 | 9/2008 | Sato |
| 2010/0136652 A1 | 6/2010 | Bieniarz et al. |
| 2010/0182877 A1 | 7/2010 | Chu |
| 2010/0184087 A1 | 7/2010 | Kosmeder et al. |
| 2011/0311123 A1 | 12/2011 | Gholap et al. |
| 2012/0129169 A1 | 5/2012 | Giovanni et al. |
| 2012/0214195 A1 | 8/2012 | Chafin et al. |
| 2012/0270293 A1 | 10/2012 | Chu |
| 2012/0329088 A1 | 12/2012 | Otter et al. |

FOREIGN PATENT DOCUMENTS

| | | |
|---|---|---|
| EP | 1605243 A1 | 12/2005 |
| EP | 1913877 A1 | 4/2008 |
| EP | 1005633 B1 | 9/2008 |
| EP | 1491156 B1 | 12/2008 |
| EP | 2278296 A1 | 1/2011 |
| WO | WO-89/07656 A2 | 8/1989 |
| WO | WO-91/03718 A1 | 3/1991 |
| WO | WO-92/07083 A1 | 4/1992 |
| WO | WO-94/07139 A1 | 3/1994 |
| WO | WO-94/09808 A1 | 5/1994 |
| WO | WO-94/15641 A1 | 7/1994 |
| WO | WO-95/06067 A1 | 3/1995 |
| WO | WO-96/40506 A1 | 12/1996 |
| WO | WO-97/00888 A1 | 1/1997 |
| WO | WO-97/26321 A2 | 7/1997 |
| WO | WO-97/36614 A1 | 10/1997 |
| WO | WO-98/01335 A1 | 1/1998 |
| WO | WO-98/20834 A2 | 5/1998 |
| WO | WO-99/09390 A1 | 2/1999 |
| WO | WO-99/53994 A1 | 10/1999 |
| WO | WO-99/66947 A1 | 12/1999 |
| WO | WO-99/67634 A1 | 12/1999 |
| WO | 2000000813 A1 | 1/2000 |
| WO | WO-2005/054811 A2 | 6/2005 |
| WO | WO-2005/121773 A1 | 12/2005 |
| WO | WO-2007/103018 A2 | 9/2007 |
| WO | 2008104564 A1 | 9/2008 |
| WO | WO-2009/007846 A2 | 1/2009 |
| WO | WO-2010/080287 A1 | 7/2010 |
| WO | WO-2011/109769 A1 | 9/2011 |
| WO | 2011071727 A2 | 12/2011 |
| WO | 2011071727 A3 | 12/2011 |
| WO | WO-2012/003476 A2 | 1/2012 |
| WO | WO-2012/110646 A1 | 8/2012 |

OTHER PUBLICATIONS

Gueuning et al., Accurate Distance Measurement by an Autonomous Ultrasonic System Combining Time-of-Flight and Phase-Shift Methods, IEEE Instrumentation and Measurement Technology Conference, Brussels, Belgium, Jun. 4-6, 1996.*

Azhari, H., "Typical Acoustic Properties of Tissues," in: Azhari, H., Basics of Biomedical Ultrasound for Engineers, (Wiley-IEEE Press, Mar. 15, 2010), pp. 313-314.

Bahr et al. "Volume Changes of Tissues in Physiological Fluids During Fixation in Osmium Tetroxide or Formaldehyde and During Subsequent Treatment," *Experimental Cell Research*, 1957, vol. 12, pp. 342-355.

Baldwin, Stephen L. et al. "Ultrasonic Detection of the Anisotropy of Protein Cross-Linking in Myocardium." Sep. 2005 IEEE Ultrasonics Symposium, vol. 4, pp. 2263-2266.

Bamber, J.C. and C.R. Hill. "Ultrasonic Attenuation and Propagation Speed in Mammalian Tissues as a Function of Temperature." *Ultrasound in Medicine & Biology*, vol. 5, pp. 149-157. Great Britain: Pergamon Press Ltd., 1979.

Bamber, J.C. et al. "Ultrasonic Propagation Through Fixed and Unfixed Tissues." *Ultrasound in Medicine & Biology*, vol. 5, pp. 159-165. Great Britain: Pergamon Press Ltd., 1979.

Berod et al., "Importance of Fixation in Immunohistochemistry," The Journal of Histochemistry and Cytochemistry, vol. 29, No. 7, Feb. 7, 1981, pp. 844-850.

Boon et al. "Formaldehyde fixation and microwave irradiation," *Histochemical Journal*, 1988, vol. 20, p. 313-322.

Bowe et al. O-GlcNAc Integrates the Proteasome and Transcriptome To Regulate Nuclear Hormone Receptors, Molecular and Celluar Biology, vol. 26, No. 22, Nov. 2006, pp. 8539-8550.

Carson, Freida L. "Fixation and Processing." in Histological Preparations: Common Problems and Their Solutions, by Richard W. Brown. Northfield, IL: College of American Pathologists, 2009, pp. 1-5.

Chartrand, Rick. "Numerical differentiation of noisy, nonsmooth data," published by Los Alamos National Laboratory, Dec. 13, 2005, p. 1-9.

Chu, Wei-Sing. "Ultrasound-accelerated Tissue Fixation / Processing Achieves Superior Morphology and Macromolecule Integrity with Storage Stability." *Journal of Histochemistry & Cytochemistry*, vol. 54(5): 503-513, 2006.

Didonato et al. "Fixation Methods for the Study of Lipid Droplets by Immunofluorescence Microscopy," *The Journal of Histochemistry & Cytochemistry*, 2003, vol. 51(6), p. 773-780.

Durgan-Yucei et al. "Rapid fixation of whole organ specimens and attendant problems," *Acta Medica Okayam*, Apr. 1992, vol. 46, Issue 2, Article 3, p. 75-81.

Engel et al., "Effects of Preanalytical on the Detection of Proteins by Immunohistochemistry in Formalin-Fixed Paraffin-Embedded Tissue," Archives of Pathology Laboratory Medicine, vol. 135, May 2011, pp. 537-543.

Fowler, et al. "Modeling formalin fixation and histological processing with ribonuclease A: effects of ethanol dehydration on reversal of formaldehyde cross links," *Laboratory Investigation*, Jul. 2008, vol. 88, p. 785-791.

Gueuning et al., "Accurate Distance Measurement by an Autonomous Ultrasonic System Combining Time-of-Flight and Phase-Shift Methods," IEEE Instrumentation and Measurement, Technology Conference, Brussels, Belgium, Jun. 4-6, 1996, pp. 399-404.

Hafajee et al. "Ultra-rapid microwave-stimulated tissue processing with a modified protocol incorporating microwave fixation," *Pathology*, 2004, vol. 36, No. 4, p. 325-329.

Hall, Christopher S. and S.A. Wickline. "High Frequency Ultrasonic Detection of Protein Cross Linking in Myocardial Tissue." 1998 IEEE Proceedings of Ultrasonics Symposium, vol. 2, pp. 1357-1360.

Hall, Christopher S. et al. "High Frequency Ultrasonic Detection of the Temporal Evolution of Protein Cross Linking in Myocardial Tissue." Jul. 2000 IEEE Transactions on Ultrasonics Ferroelectrics & Frequency Control 47(4): 1051-8.

Hamberg et al. "A novel method for the detection of porcine circovirus type 2 replicative double stranded viral DNA and nonreplicative single stranded viral DNA in tissue sections," *J. Vet. Diagn. Invest.*, 2007, vol. 19, p. 135-141.

Hill, C.R. et al., editors, Physics Department, Institute of Cancer Research, Royal Marsden Hopspital, Sutton, Surrey, UK. *Physical Principles of Medical Ultrasonics*, second edition. Chichester, England: John Wiley & Sons Ltd., 2004. 518 pages.

Hoffmeister, B.K. et al. "Estimation of the elastic stiffness coefficient $c_{13}$ of fixed tendon and fixed myocardium." *Journal of the Acoustical Society of America* 97(5), May 1995, pp. 3171-3176.

Holczinger. "Formation of aldehyde groups in tissues after formal fixation," *Acta Histochem*, 1958, vol. 6(1-4), p. 36-43.

Holt et al, "Studies on Formalin Fixation for Electron Microscopy and Cytochemical Staining Purposes," *The Journal of Biophysical and Biochemical Cytology*, 1961, vol. 11, p. 31-45.

Hopwood, "Microwaves and Heat in Aldehyde Fixation: Model Experiments with Bovine Serum Albumin," *Methods: A Companion to Methods in Enzymology*, 1998, vol. 15, p. 119-122.

(56) References Cited

OTHER PUBLICATIONS

Ichimura et at. "Formaline fixation by boiling: is it suitable for the TUNEL staining?" *Pathol. Int.* 1995, vol. 45, No. 12, p. 971-972.
Iesurum et al. "Microwave Processing and Ethanol-Based Fixation in Forensic Pathology," *The American Journal of Forensic Medicine and Pathology*, Jun. 2006, vol. 27, No. 2, p. 178-182.
European Patent Office Searching Authority, International Search Report and Written Opinion, PCT Application No. PCT/EP2012/052800, dated Jul. 2, 2012, 13 pages.
European Patent Office Searching Authority, International Search Report, counterpart PCT Application No. PCT/US2011/027284, dated Jul. 1, 2011, 3 pages.
European Patent Office Searching Authority, Written Opinion, counterpart PCT Application No. PCT/US2011/027284, dated Sep. 4, 2012, 6 pages.
Koshiba et al. "The Effect of Formalin Fixation on DNA and the Extraction of High-molecular-weight DNA from Fixed and Embedded Tissues," *Path. Res. Pract.*, 1993, vol. 189, p. 66-72.
Lagerstedt, "The effect of formaldehyde-fixation on the amount of ultraviolet absorbing substances related from tissue sections in the histochemical ribonuclease test," *Z Zellfrosch Mikrosk Anta.*, 1957, vol. 45(4), p. 472-482.
Lampton, Michael. "Damping-Undamping Strategies for the Levenberg-Marquardt Nonlinear Least-Squares Method," *Computers in Physics*, vol. 11, No. 1, Jan./Feb. 1997, p. 110-115.
Lawson, Alison et al. "Cytotoxicity Effects of Cryoprotectants as Single-Component and Cocktail Vitrification Solutions," Author Manuscript published in *Cryobiology*, Apr. 2011, 18 pages.
Lowry et al. "Immunohistochemical methods for semiquantitative analysis of collagen content in human peripheral nerve," *J. Anat.*, 1997, vol. 191, p. 367-374.
Manger et al. "Acquisition of brains from the African elephant (*Loxodonta Africana*): Perfusion-fixation and dissection," *Journal of Neuroscience Methods*, 2009, vol. 179, p. 16-21.
Manning et al. "Simultaneous Formalin Fixation and EDTA Decalcification, with Carbowax Embedding for Preservation of Acid Phosphatase," *Stain Technology*, 1965, p. 7-12.
Marioli et al., "Digital Time-of-Flight Measurement for Ultrasonic Sensors," *IEEE Transactions of Instrumentation and Measurement*, vol. 41, No. 1, Feb. 1992, pp. 93-97.
Marutyan et al., "The Frequency Dependence of Ultrasonic Velocity and the Anisotropy of Dispersion in Both Freshly Excised and Formalin-Fixed Myocardium," Ultrasound in Medicine and Biology, vol. 32, No. 4, Apr. 2006, pp. 603-610.
Mathews et al., "Shaping policy: the Canadian Cancer Society and the Hormone Receptor Testing Inquiry," Current Oncology, vol. 18, No. 4, Aug. 2008, pp. 174-179.
Middleton et al., "Implementation of American Society of Clinical Oncology/College of American Pathologists HER2 Guideline Recommendations in a Tertiary Care Facility Increases HER2 Immunohistochemistry and Fluorescence In Situ Hybridization Concordance and Decreases the Number of Inconclusive Cases," Archives of Pathology Laboratory Medicine, vol. 133, May 2009, pp. 775-780.
Noguchi et al. "Modified formalin and methanol fixation methods for molecular biological and morphological analyses," *Pathology International*, 1997, vol. 47, p. 685-691.

Plebani et al., "Mistakes in a stat laboratory: types and frequency," Clinical Chemistry, vol. 43, No. 8, Aug. 1997, pp. 1348-1351.
Puchtler, H. and S.N. Meloan. "On the chemistry of formaldehyde fixation and its effects on immunohistochemical reactions." *Histochemistry* (1985) 82:201-204.
Rait et al. "Modeling formalin fixation and antigen retrieval with bovine pancreatic ribonuclease A: I-Structural and functional alterations," *Laboratory Investigation*, 2004, No. 84, p. 292-299.
Rait et al. "Modeling formalin fixation and antigen retrieval with bovine pancreatic RNase A II. Interrelationship of cross-linking, immunoreactivity, and heat treatment," *Laboratory Investigation*, 2004, vol. 84, p. 300-306.
Ruijter et al. "Rapid Microwave-Stimulated Fixation of Entire Prostatectomy Specimens," *Journal of Pathology*, 1997, vol. 183, pp. 369-375.
Sarvazyan et al., "Ultrasonic Assessment of Tissue Hydration Status," Ultrasonics, vol. 43, No. 8, Aug. 2008, pp. 661-671.
Shibutani et al. "Methacarn Fixation: A Novel Tool for Analysis of Gene Expressions in Paraffin-Embedded Tissue Specimens," The United States and Canadian Academy of Pathology, Inc., Laboratory Investigation vol. 80, No. 2 Copyright 2000, pp. 199-208.
Srinivasan et al. "Effect of Fixatives and Tisse Processing on the Content and Integrity of Nucleic Acids," American Journal of Pathology, vol. 161, No. 6, Dec. 2002, pp. 1961-1971.
Svilainis et al., "The time-of-flight estimation accuracy versus digitization parameters," ULTRAGARSAS (Ultrasound), vol. 63, No. 1, 2008 pp. 12-17.
Van Valkenburg et al. "The use of microwave irradiation with low formalin concentration to enhance the conversion of dopamine into norsasolinol in rat brain: a pilot study," *Histochemical Journal*, 1990, vol. 22, pp. 353-357.
Walker et al. "The Use of Formalin Fixation in the Cytochemical Demonstration of Succinic and DPN- and TPN-Dependent Dehydrogenases in Mitchondria," *The Journal of Cell Biology*,1963, vol. 16, pp. 455-469.
Wolff et al., "American Society of Clinical Oncology/College of American Pathologists Guideline Recommendations for Human Epidermal Growth Factor Receptor 2 Testing in Breast Cancer," Archives of Pathology Laboratory Medicine, vol. 135, Jan. 2007, pp. 18-43.
Wolff, Antonio C. et al. "American Society of Clinical Oncology/College of American Pathologists Guideline Recommendations for Human Epidermal Growth Factor Receptor 2 Testing in Breast Cancer," *Journal of Clinical Oncology ASCO Special Article*, vol. 25, No. 1, Jan. 1, 2007, pp. 118-145.
Zeikus et al. "Use of Hot Formaldehyde Fixative in Processing Plant-Parasitic Nematodes for Electron Microcopy," *Stain Technology*, 1975, vol. 50, No. 4, p. 219-225.
Zimmermann, K.P. et al., University of Missouri. "On velocity changes caused by tissue fixation," Letters to the Editor in *Ultrasound in Medicine & Biology*, vol. 10, No. 4, Jul.-Aug. 1984. 6 pages.
NDT Resource Center, "Attenuation of Sound Waves" www.nde-ed.org/EducationResources/CommunityCollege/Ultrasonics/Physics/attenuation.htm(last accessed Nov. 25, 2014).
Peracchia et al., New Glutaraldehyde Fixation Procedures, J. Ultrastructure Research 39, 57-64 (1972).

\* cited by examiner

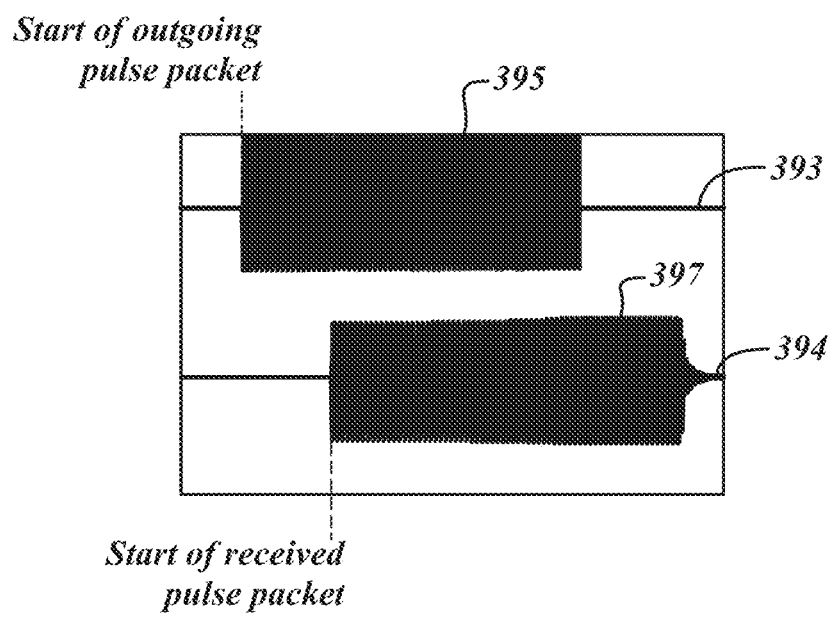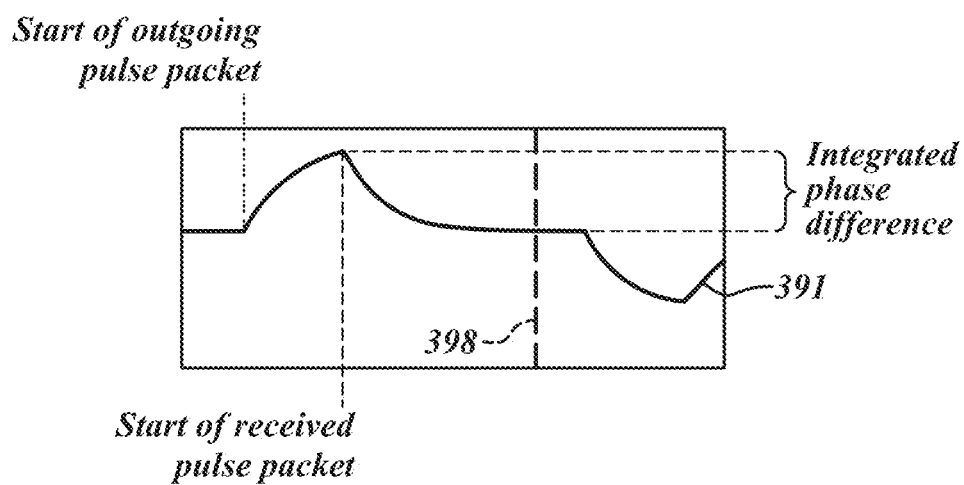
FIG. 9

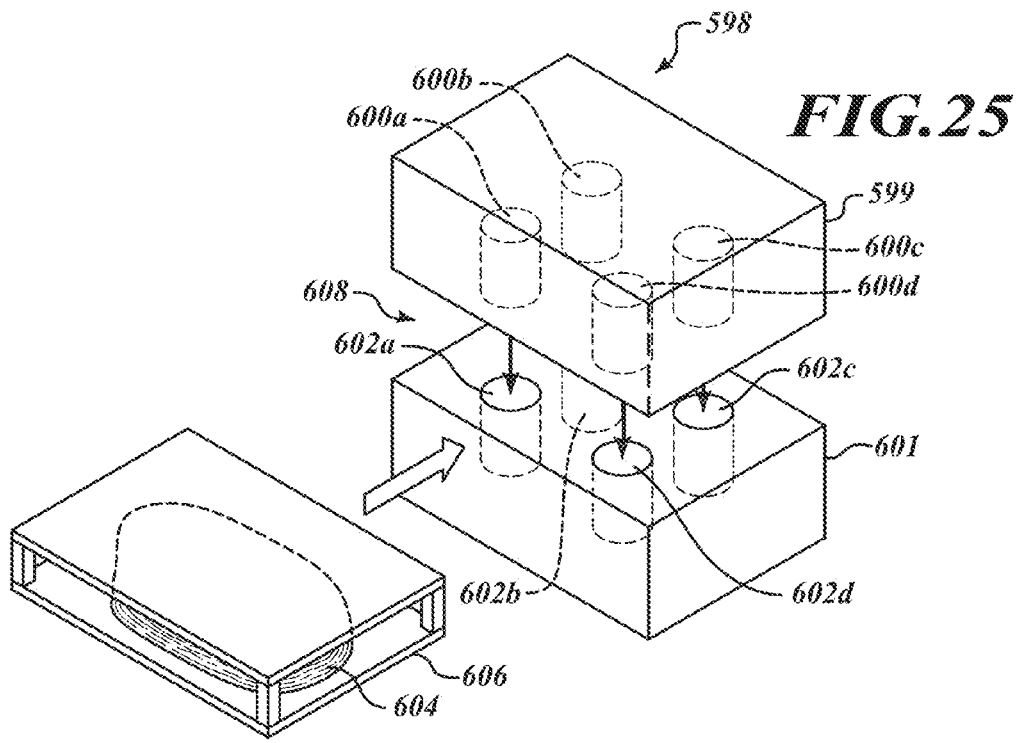
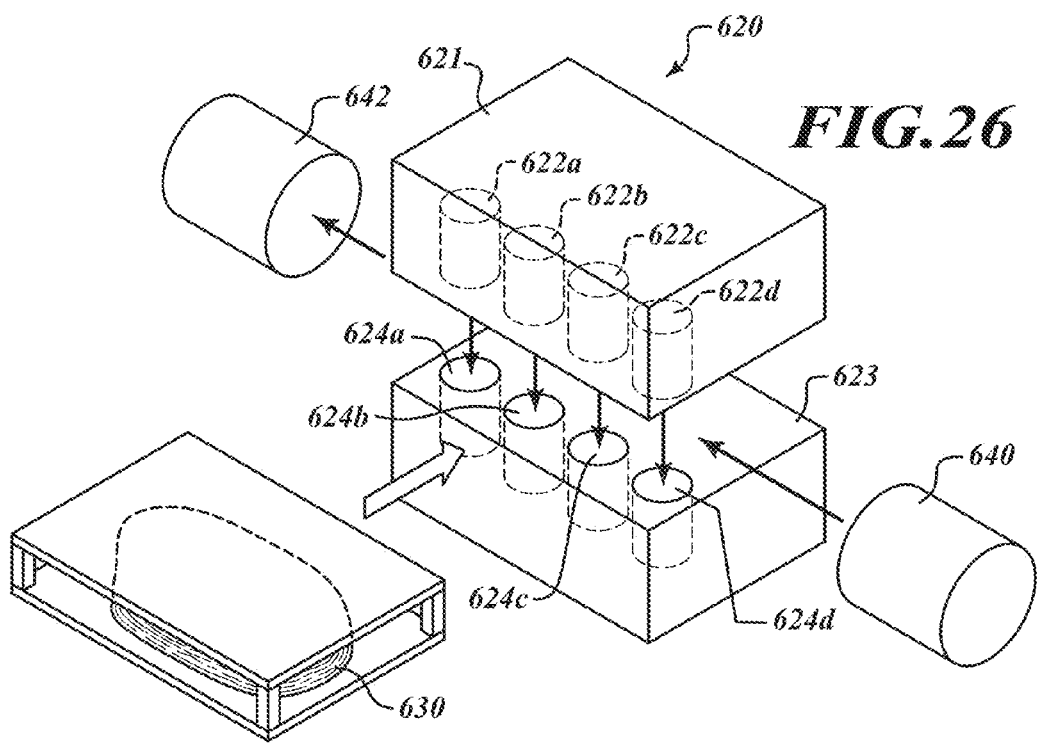

SYSTEMS AND METHODS FOR MONITORING TISSUE SAMPLE PROCESSING

CROSS-REFERENCE TO RELATED APPLICATIONS

The present application is a continuation-in-part under 35 U.S.C. § 120 of U.S. application Ser. No. 13/372,040, filed on Feb. 13, 2012, which is a continuation-in-part of International Application No. PCT/US2011/027284, filed on Mar. 4, 2011 (now converted to U.S. application Ser. No. 13/582,705, filed Sep. 4, 2012), which claims benefit under 35 U.S.C. § 119(e) of U.S. provisional application Ser. No. 61/310,653, filed on Mar. 4, 2010; and U.S. application Ser. No. 13/372,040 also claims benefit under 35 U.S.C. § 119(e) of U.S. provisional application Ser. No. 61/464,479, filed on Mar. 4, 2011, and U.S. provisional application Ser. No. 61/463,551, filed on Feb. 17, 2011. All of these prior applications are incorporated herein by reference in their entireties.

TECHNICAL FIELD

The present disclosure relates generally to systems and methods for analyzing specimens. More specifically, the present disclosure relates to methods and systems for monitoring processing of tissue samples.

BACKGROUND

Preservation of tissues from surgical procedures is currently a topic of great importance. Currently, there are no standard procedures for fixing tissues and this lack of organization leads to a variety of staining issues both with primary and advanced stains. The first step after removal of a tissue sample from a subject is to place the sample in a liquid that will suspend the metabolic activities of the cells. This process is commonly referred to as "fixation" and can be accomplished by several different types of liquids. The most common fixative in use by anatomical pathology labs is 10% neutral buffered formalin (NBF). This fixative forms cross-links between formaldehyde molecules and amine containing cellular molecules. In addition, this type of fixative preserves proteins for storage.

When used at room temperature, NBF diffuses into a tissue section and cross-links proteins and nucleic acids, thereby halting metabolism, preserving biomolecules, and readying the tissue for paraffin wax infiltration. The formalin can be at slightly elevated temperature (i.e., higher than room temperature) to further increase the cross-linking rate, whereas lower temperature formalin can significantly decrease the cross-linking rate. For this reason, histologists typically perform tissue fixation at room temperature or higher. Some groups have used cold formalin, but only in specialized situations and not for fixing tissues. For instance, cold formalin has been used to examine lipid droplets.

Several effects are often observed in tissues that are either under exposed or over exposed to formalin. If formalin has not diffused properly through the tissue samples, outer regions of the tissue samples exposed to formalin may be over-fixed and interior regions of the tissue samples not exposed to formalin may be under-fixed, resulting in very poor tissue morphology. In under-fixed tissue, subsequent exposure to ethanol often shrinks the cellular structures and condenses nuclei since the tissues will not have the chance to form a proper cross-linked lattice. When under-fixed tissue is stained, such as with hematoxylin and eosin (H&E), many white spaces may be observed between the cells and tissue structures, nuclei may be condensed, and samples may appear pink and unbalanced with the hematoxylin stain. Tissues that have been exposed to excess amounts of formalin or too long typically do not work well for subsequent immunohistochemical processes, presumably because of nucleic acid and/or protein denaturation and degradation. As a result, the optimal antigen retrieval conditions for these tissues do not work properly and therefore the tissue samples appear to be under stained.

Proper medical diagnosis and patient safety often require properly fixing the tissue samples prior to staining. Accordingly, guidelines have been established by oncologists and pathologists for proper fixation of tissue samples. For example, according to the American Society of Clinical Oncology (ASCO), the current guideline for fixation time in neutral buffered formalin solution for HER2 immunohistochemistry analysis is at least 6 hours, preferably more, and up to 72 hours. It may be advantageous to develop a process for monitoring diffusion of fixatives through a tissue sample to determine whether the fixative has infused the entire tissue sample to minimize or limit under-fixed tissue or over-fixed tissue and to better preserve biological molecules, tissue morphology, and/or post-translational modification signals before significant degradation occurs.

Overveiw of Disclosure

At least some embodiments disclosed herein are methods of preparing specimens for a fixation process. Specimens, such as solid tissue samples, can be contacted with a liquid fixative that travels through the tissue samples. The fixative can be allowed to diffuse throughout substantially the entire thickness of the tissue samples. After a sufficient amount of fixative has infused the tissue samples, a fixation process can be performed to fix substantially all of the tissue, thereby minimizing or limiting under-fixation and over-fixation in, for example, outer regions and inner regions. The method can enhance the quality in preservation of tissue methodology, protein structure, and/or post-translation modification signals.

At least some embodiments disclosed herein are methods and systems for analyzing a tissue sample based on its characteristics, including acoustic characteristics, mechanical characteristics, optical characteristics, or other characteristics that may be static or dynamic during processing. In some embodiments, acoustic properties of the tissue sample are continuously or periodically monitored to evaluate the state and condition of the tissue sample throughout processing. Based on the obtained information, processing can be controlled to enhance processing consistency, reduce processing times, improve processing quality, or the like.

Acoustics can be used to non-invasively analyze tissue samples. When an acoustical signal interacts with tissue, transmitted signals (e.g., signals transmitted through the tissue sample) depends on several mechanical properties of the sample, such as elasticity and firmness. The acoustic properties of tissue samples may change as liquid reagent (e.g., a liquid fixative) travels through the sample. In some procedures, acoustic properties of the tissue sample can change as interstitial fluid is displaced with liquid reagent because of different acoustic properties between the interstitial fluid and liquid reagent. Even though fixatives may not result in substantial cross-linking, the acoustic properties of the tissue sample can change as the fixative travels across the thickness of the sample. The sample's acoustic properties can change during, for example, a pre-soak process (e.g., diffusion of cold fixative), a fixation process, a staining process, or the like. In the fixation process (e.g., a cross-linking process), the speed of transmission of acoustic energy can change as the tissue sample becomes more heavily cross-linked.

In some embodiments, a method for tissue preparation can include contacting a tissue sample with a fixative. Real-time monitoring can be used to accurately track movement of the fixative through the sample. After the fixative has diffused through the tissue sample, a fixation process and a subsequent histological process can be performed. A status of a biological sample can be monitored based on a time of flight of acoustic waves. The status can be a diffusion status, a density status, a fixation status, a staining status, or the like. Monitoring can include, without limitation, measuring changes in a level of diffusion, sample density, cross-linking, decalcification, stain coloration, or the like. The biological sample can be solid or non-fluidic tissue, such as bone, or other type of tissue.

In some embodiments, methods and systems are directed to using acoustic energy to monitor a tissue sample. Based on interaction between the acoustic energy in reflected and/or transmission modes, information about the specimen may be obtained. Examples of measurements include acoustic signal amplitude, attenuation, scatter, absorption, time of flight (TOF) in the specimen, phase shifts of acoustic waves, or combinations thereof. In some procedures, a fixative is applied to the specimen. As the fixative diffuses through the specimen, the tissue sample's mechanical properties (e.g., elasticity, stiffness, etc.) change, and these changes can be monitored using sound speed measurements via TOF. Subsequent processes can be monitored based on TOF and a state of the specimen (e.g., a state of saturation, a fixative state, a histological state, etc.) can be determined. To avoid under-fixation or over-fixation, the static characteristics of the tissue (including reagent(s) in the tissue), dynamic characteristics of the tissue, or both can be monitored. Characteristics of the tissue include transmission characteristics, reflectance characteristics, absorption characteristics, attenuation characteristics, or the like.

In some procedures, an unfixed tissue sample is contacted with a fixative. The movement of the fixative through the tissue sample can be monitored in real-time. The composition of the fixative can be selected to enhance monitoring. For example, NBF has a relatively high bulk modulus compared to interstitial fluid. The sound transmissibility of the fixative is related to its bulk modulus (k) and density (p) according to the speed equation, $$\text{speed of sound in fixative} = \sqrt{\frac{k}{p}}.$$

The fixative, such as formalin, with a bulk modulus greater than interstitial fluid can significantly alter the TOF as it displaces the interstitial fluid. Once a desired level of diffusion is achieved, the tissue sample can be removed from the fixative to generally stop further diffusion. The tissue sample, including the fixative within the tissue sample, can be heated to promote cross-linking and fixation.

A TOF acquisition scheme can be used to monitor tissue samples. The TOF acquisition scheme can include an ND conversion scheme (e.g., about 1 μsec phase comparison) to obtain a large number of phase comparisons to provide generally real-time monitoring. The phase comparisons can be performed at the same frequency and phase relationship, and the temperature of the fixative and/or tissue sample can remain generally constant to increase signal to noise ratios. Because fluctuations in temperature may cause measureable changes in TOF, the TOF acquisition scheme can compensate for changes in TOF attributable to, for example, temperature changes.

In some embodiments, a method for evaluating tissue sample includes contacting tissue sample with a reagent. Diffusion of the reagent through the tissue sample can be monitored based on properties of the tissue sample, including mechanical properties, acoustic properties, and/or optical properties. Monitoring includes, without limitation, measuring time of flight of acoustic waves that travel through a tissue sample. This monitoring can include, transmitting acoustic waves across a thickness of the sample while a reagent gradually moves across the tissue sample. After the reagent in the form of fixative has diffused through most of the volume of the tissue sample, a fixation process is performed. For example, the fixative can diffuse through at least 90% by volume of the tissue sample. In other embodiments, the fixative can diffuse through substantially all the volume of the tissue sample. In one procedure, the fixative can diffuse through at least 95% by volume of the tissue sample. Such processes can substantially eliminate over-fixation or under-fixation of interior and outer regions of tissue samples.

In some embodiments, a processing method comprises contacting a tissue sample, which is in an unfixed state, with a liquid fixative. The movement of the liquid fixative through a tissue sample is acoustically monitored. A fixation process can be performed after the liquid fixative has displaced a target volume of interstitial fluid from the tissue sample. In one procedure, the fixation process is performed after the liquid fixative has displaced at least 50% by volume of the interstitial fluid. In other procedures, the fixation process is performed after the fixative has displaced at least 75% by volume of the interstitial fluid. Such fixation processes can include heating the tissue sample to promote cross-linking.

A processing system, in some embodiments, comprises an acoustic monitoring device and a computing device communicatively coupled to the acoustic monitoring device. The acoustic monitoring device can detect acoustic waves that have traveled through a tissue sample. The computing device can be configured to evaluate the speed of an acoustic wave traveling through the tissue sample based on time of flight. The computing device, in some embodiments, includes instructions for monitoring diffusion of a liquid using the acoustic monitoring device and for performing a fixation process. The acoustic monitoring device, in some embodiments, includes one or more transmitters and one or more receivers. The tissue sample can be immersed in a liquid fixative while the transmitters and receivers communicate to detect time of flight of acoustic waves.

In some embodiments, a method of evaluating a tissue sample comprises contacting the tissue sample with a fixative. The movement of the fixative through the tissue sample can be monitored based on the acoustic waves. In certain procedures, the monitoring can include simultaneously monitoring diffusion and cross-linking performed at the same or different processing temperatures. For example, diffusion and cross-linking can be performed while a fixative and/or a tissue sample is maintained at the same general temperature. In other procedures, the diffusion and cross-linking can be performed at different temperatures.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

FIG. 9 is a plot showing a timing relationship between an outputted signal, a received signal, and a comparison curve.

FIG. 25 is an isometric view of an analyzer ready to receive a specimen holder.

FIG. 26 is an isometric view of an analyzer with a linear array of transmitters and a linear array of receivers.

DETAILED DESCRIPTION

Figure 1:
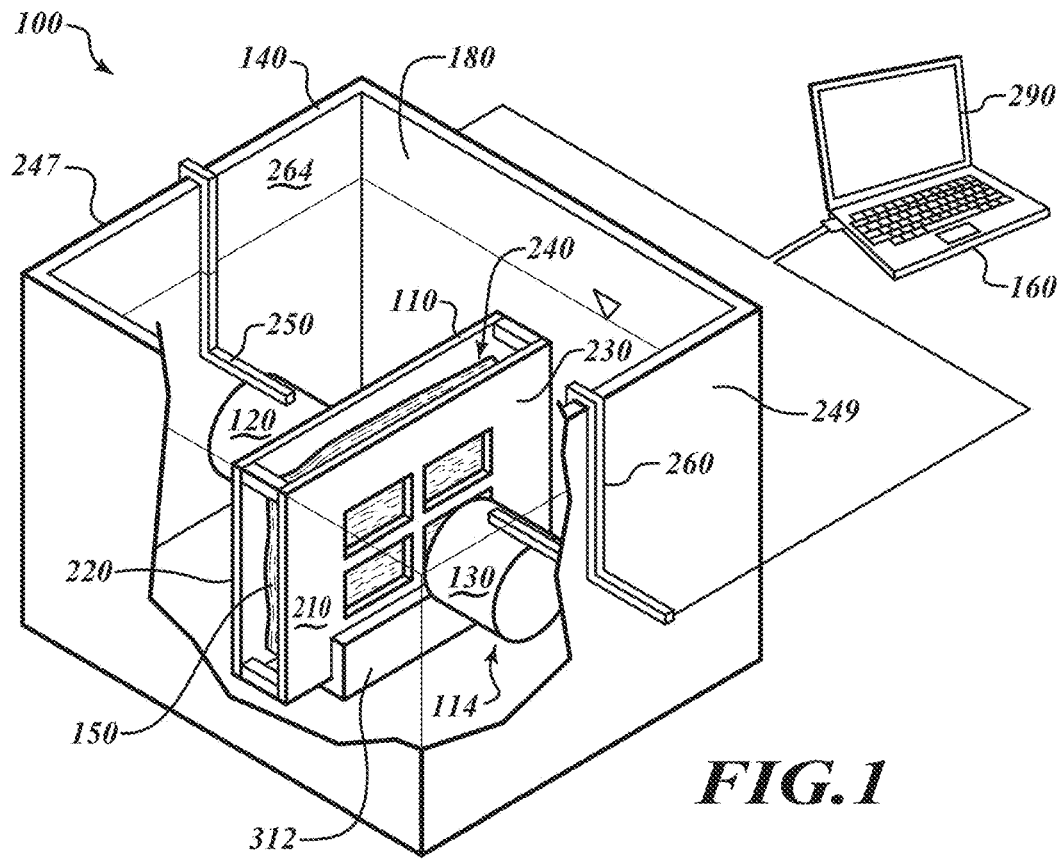
FIG. 1 is an isometric, cutaway view of a processing system containing a specimen holder with a specimen, in accordance with one embodiment.

At least some embodiments of the present disclosure are directed to monitoring a multi-step tissue preparation process that includes, without limitation, a fixative delivery process ("delivery process") and a fixation/cross-linking process ("fixation process"). The delivery process can include contacting the tissue sample with a liquid fixative at a first temperature for a first period of time. Movement of the fixative can be monitored to evaluate whether the fixative has adequately infused the sample. After desired diffusion is achieved, the tissue sample can be heated to a second temperature higher than the first temperature to start or promote cross-linking. If the fixative is formaldehyde, cross-linking can occur between formaldehyde molecules and amine containing cellular molecules without significantly compromising the tissue characteristics (e.g., antigenicity and/or morphology).

The delivery process can involve diffusion of cold fixative throughout substantially the entire thickness or cross section of the tissue sample. The cold fixative can be at a temperature in a range of about −20° C. to about 15° C., preferably greater than 0° C. to an upper temperature more typically about 10° C., and even more preferably from about 3° C. to about 5° C. For some procedures, the fixative temperature can be about 4° C. However, the cold fixative can be at other temperatures. The delivery time period can be in a range of about 15 minutes up to about 4 hours, most typically from greater than 15 minutes to about 3 hours, with desirable results typically being obtained by immersing tissue samples for about 1.5 hours to about 2 hours. Increasing the delivery time period to 4 hours or greater may have little beneficial effect for smaller tissue pieces with thicknesses up to about, for example, 4 mm. Additionally, the composition of the fixative can be selected to achieve a desired diffusion coefficient. Example fixatives include aldehyde fixatives, such as 10% NBF or 20% NBF. Table 1 below shows diffusion rate constants for cores of tonsil tissue with about 6 mm thicknesses. The diffusion rate at a temperature of 4° C. through 6 mm cores of tonsil tissue can be approximated by diffusion equations or diffusion modeling.

TABLE 1

| NBF Concentrations | Rate Constant C (at 4 C./6 mm core) | Time to reach 50% [hours] | to reach 95% [hours] |
| --- | --- | --- | --- |
| 10% | 0.00015 | 1.3 | 5.5 |
| 20% | 0.0002 | 1.0 | 4.2 |
| 40% | 0.00025 | 0.8 | 3.3 |

Table 1 shows that 40% NBF can diffuse through about 50% of the volume of the 6 mm core tissue specimen in about 0.8 hour and about 95% of the tissue sample in about 3.3 hours. The 20% NBF can diffuse through about 50% of the volume of the tissue specimen in about 1.3 hours and about 95% of the tissue sample in about 5.5 hours. Accordingly, to reduce processing times, the concentration of NBF can be increased to increase the rate of diffusion Although some cross-linking may occur during the delivery process, the cross linking primarily occurs after the delivery process (i.e., during the fixation process). The delivery process can be performed to balance the beneficial properties associated with substantially complete diffusion while minimizing or limiting the effects associated with initializing or promoting cross-linking. In some embodiments, the rate of diffusion can be maximized while limiting and minimizing any deleterious effects associated with increased cross-linking rate.

To perform the fixation process, the tissue sample can be removed from the cold fixative and immersed in warm fixative to start cross-linking and/or increase the rate of cross-linking. The temperature of the warm fixative can be greater than the ambient temperature and up to at least 55° C., more typically from about 35° C. to about 45° C., as this temperature range may increase the cross-linking kinetics sufficiently to allow relatively quick tissue cross-linking. However, if the temperature is increased above about 50° C., the tissue sample may begin to degrade, which may have a deleterious effect on certain subsequent histological reactions. Thus, the upper temperature and time period of the fixation process can be selected to allow subsequent imaging processes, such as in situ hybridization, IHC, H&E, western blotting, PCR, and/or sequencing and nucleic acid analysis. The time period for the fixation process can range from greater than about 15 minutes up to at least about 5 hours, more typically is at least about 1 hour to about 4 hours, and more typically is from about 2 hours to about 3 hours. In certain embodiments, the fixation process can be performed for about 1.5 hour at a temperature of about 45° C.

The fixatives in the delivery process and the fixation process can be the same or different. As yet another example, entirely different aldehyde fixatives, such as formaldehyde and glutaraldehyde, can be used for the delivery and fixation processes. Additionally, instead of removing the sample from the fixative, the fixative can be heated for fixation. As such, the tissue sample can remain immersed in the same fixative throughout the diffusion and fixation processes.

Various factors may be considered to determine processing conditions for a particular tissue sample. These factors can include: sample thickness, which typically ranges from about 1 mm to about 10 mm thick, more typically from about 2 mm to about 8 mm thick, and even more typically from about 4 mm to about 6 mm thick; volume of fixative to tissue sample mass, which typically is from about 10:1 to about 50:1 volume to mass; fixative composition; temperature; and sample immersion time in the fixative. Other factors can also be considered to determine processing conditions.

FIG. 1 shows a processing system 100 for processing specimens. The processing system 100 includes a specimen holder 110, a container 140, and an analyzer 114 positioned in the container 140. The analyzer 114 includes a transmitter 120 and a receiver 130. A computing device 160 is communicatively coupled to the analyzer 114.

Figure 2:
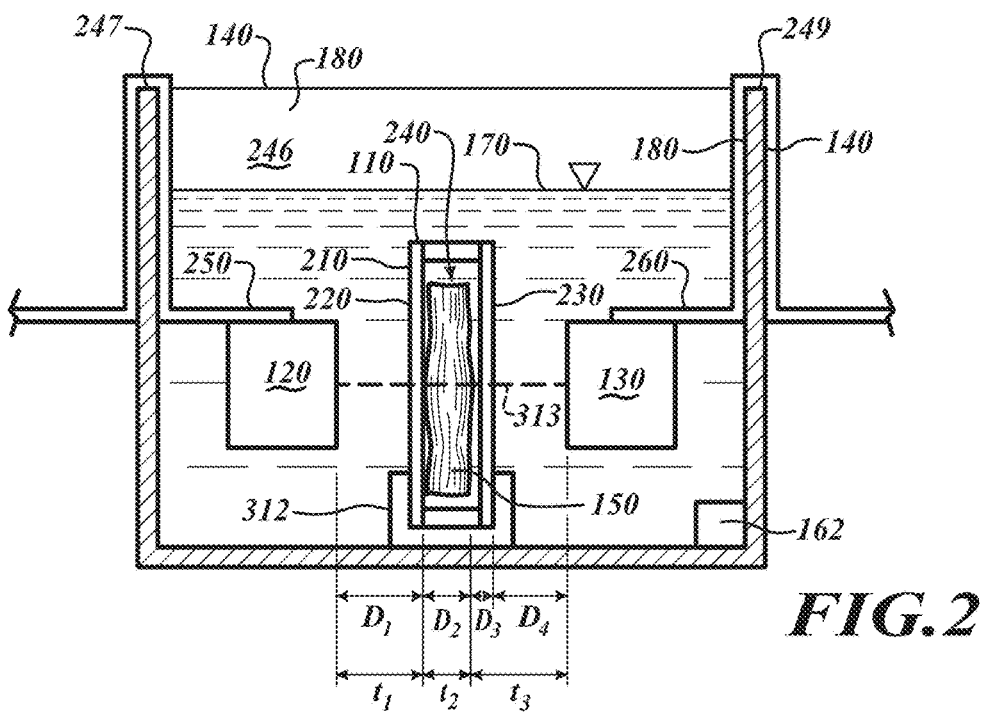
FIG. 2 is a side cross-sectional view of components of the processing system of FIG. 1.

FIG. 2 shows the container 140 with a chamber 180 filled with a processing media 170. The specimen holder 110, the transmitter 120, and the receiver 130 are submerged in the processing media 170. A thermal device 162 can increase or decrease the temperature of the media 170 to, for example, perform processes at different temperatures. The thermal device 162 can include, without limitation, one or more refrigeration systems, heaters (e.g., resistance heaters, electric heaters, etc.), thermoelectric devices (e.g., Peltier devices), or the like.

To presoak a tissue sample 150, the processing can be a cold fixative at a temperature in a range of about 0° C. to about 5° C. The computing device 160 can cause the transmitter 120 to output energy that passes through the specimen 150. The receiver 130 can receive the energy and can send signals to the computing device 160 in response to the received energy. The computing device 160 analyzes those signals to monitor processing. Once processing is complete, the specimen holder 110 can be conveniently removed from the container 140 or the processing media 170 can be deactivated. After the desired level of diffusion is achieved, the thermal device 162 can increase the average temperature of the media 170 to promote cross-linking. Once fixation is achieved, the sample 150 can be removed from the media 170.

The specimen 150 can be one or more biological samples. A biological sample can be a solid tissue sample (e.g., any collection of cells) removed from a subject. In some embodiments, a biological sample is mountable on a microscope slide and includes, without limitation, a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can be used to obtain the sample. A freshly removed tissue sample can be placed in the processing media 170 within an appropriate amount of time to prevent or limit an appreciable amount of degradation of the sample 150. In some embodiments, the sample 150 is excised from a subject and placed in the media 170 within a relatively short amount of time (e.g., less than about 2 minutes, 5 minutes, 30 minutes, 1 hour, 2 hours, or the like). Of course, the tissue sample can be fixed as soon as possible after removal from the subject. The specimen 150 can also be frozen or otherwise processed before fixation.

To analyze the specimen 150 using acoustic energy, the transmitter 120 can output acoustic waves. The acoustic waves can be infrasound waves, audible sound waves, ultrasound waves, or combinations thereof. Propagation of the acoustic waves through the specimen 150 may change because of changes to the specimen 150. If the process involves diffusion, the acoustic properties of the specimen 150 can change as the media 170 infuses the specimen 150. If the process involves cross-linking, mechanical properties (e.g., an elastic modulus) of the specimen 150 may change significantly as cross-linking progresses through the tissue. The change in elastic modulus may alter the acoustic characteristics of the specimen 150. Acoustic characteristics include, without limitation, sound speeds, transmission characteristics, reflectance characteristics, absorption characteristics, attenuation characteristics, or the like. To evaluate transmission characteristics, a time of flight of sound (e.g., audible sound, ultrasound, or both), the speed of sound, or the like can be measured. The TOF is a length time that it takes for acoustic waves to travel a distance through an object or substance. In some embodiments, the TOF is the length of time it takes acoustic waves to travel through a specimen in comparison to the time to travel through the medium displaced by the specimen. In some embodiments, the time of flight of the medium and the measurement device (e.g., the holder) may be recorded prior to insertion of the sample and stored for later reference so that it can be used for temperature compensation, evaporative losses, compensation protocols, predictive modeling, or the like. The thickness of the specimen 150 can be sufficiently large to produce a measurable change in the TOF. In reflectance embodiments, the TOF can be the length of the time the acoustic waves travel through a portion of the tissue sample. For example, the TOF may be the length of time that the acoustic waves propagate within a portion of the tissue sample. Thus, the TOF can be calculated based on acoustic waves that travel through the entire specimen, acoustic waves reflected by the tissue sample, or both.

The speed of acoustic waves traveling through the specimen 150 is generally equal to the square root of a ratio of the elastic modulus (or stiffness) to the density of the specimen 150. The density of the specimen 150 may remain generally constant and, thus, changes in the speed of sound and the changes in TOF are primarily due to changes in the specimen's elastic modulus. If the density of the specimen 150 changes a significant amount, the sound speed changes and the TOF changes attributable to a change in elastic modulus can be determined by considering the specimen's changing density. Thus, both static and dynamic characteristics of the specimen 150 can be analyzed.

The processing system 100 can be a closed loop system or an open loop system. In closed loop embodiments, acoustic energy is transmitted through the specimen 150 based upon feedback signals from the receiver 130 and/or signals from one or more sensors configured to detect a parameter (e.g., temperature, pressure, or any other measurable parameter of interest) and to transmit (or send) signals indicative of the detected parameter. Based on those signals, the processing system 100 can control operation of the transmitter 120. Alternatively, the processing system 100 can be an open loop system wherein the transmitted acoustic energy is set by, for example, user input. It is contemplated that the processing system 100 can be switched between a closed loop mode and an open loop mode.

The specimen holder 110 can be portable for conveniently transporting it between various locations. In a laboratory setting, a user can manually transport it between workstations or between equipment. The illustrated specimen holder 110 is in the form of a cassette with a rigid main body 210 that surrounds and holds the specimen 150. The main body 210 includes a first plate 220 and a second plate 230 spaced apart from the first plate 220 to define a receiving space or chamber 240. The specimen 150 is positioned in the receiving space 240. The plates 220, 230 can have apertures or other features that facilitate transmission of acoustic energy. The shape, size, and dimensions of the specimen holder 110 can be selected based on the shape, size, and dimensions of the specimen 150. In various embodiments, the specimen holder can be (or include) a cassette, a rack, a basket, a tray, a case, foil, fabric, mesh, or any other portable holder capable of holding and transporting specimens. In some embodiments, the specimen holder 110 is a standard biopsy cassette that allows fluid exchange.

With continued reference to FIGS. 1 and 2, the transmitter 120 and the receiver 130 are fixedly coupled to walls 247, 249 of the container 140 by brackets 250, 260, respectively. The container 140 can be a tank, a tub, a reservoir, a canister, a vat, or other vessel for holding liquids and can include temperature control devices, a lid, a covering, fluidic components (e.g., valves, conduits, pumps, fluid agitators, etc.), or the like. To pressurize the processing media 170, the chamber 180 can be a pressurizable reaction chamber. Additionally the chamber 180 can be operated under a vacuum to reduce air bubble formation impeding sound transmission, and to support easier perfusion of fluids into the specimen holder 110 to displace trapped air.

To minimize, limit, or substantially eliminate signal noise, the container 140 can be made, in whole or in part, of one or more energy absorbing materials (e.g., sound absorbing materials, thermally insulating materials, or the like). The size and shape of the container 140 can be selected to prevent or substantially eliminate unwanted conditions, such as standing waves, echoing, or other conditions that cause signal noise. For example, if acoustic waves reflect off the inner surfaces of the container 140 and result in signal noise, the size of the container 140 can be increased.

The transmitter 120 can include a wide range of different types of acoustic elements that can convert electrical energy to acoustic energy when activated. For example, an acoustic element can be a single piezoelectric crystal that outputs a single waveform. Alternatively, an acoustic element may include two or more piezoelectric crystals that cooperate to output waves having different waveforms. The acoustic elements can generate acoustic waves in response to drive signals from the computing device 160 and can output at least one of audible sound waves, ultrasound waves, and infrasound waves with different types of waveforms. The acoustic waves can have sinusoidal waveforms, step waveforms, pulse waveforms, square waveforms, triangular waveforms, saw-tooth waveforms, arbitrary waveforms, chirp waveforms, non-sinusoidal waveforms, ramp waveforms, burst waveforms, pulse compression waveforms (e.g., window chirped pulse compression waveforms), or combinations thereof. In some embodiments, the acoustic elements are transducers capable of outputting and detecting acoustic energy (e.g., reflected acoustic energy). Such embodiments are well suited to evaluate the specimen based on reflected acoustic waves. For example, the transmitter 120 can be in the form of an ultrasound transducer that transmits acoustic waves through at least a portion of the tissue sample 150. At least some of the acoustic waves can be reflected from the tissue sample 150 and received by the ultrasound transducer 120. A wide range of different signal processing techniques (including cross-correlation techniques, auto-correlation techniques, echoing analysis techniques, phase difference analysis, integration techniques, compensation schemes, synchronization techniques, etc.) can be used to determine a TOF of the acoustic waves. The computing device 160 can thus evaluate acoustic energy that is transmitted through the entire specimen 150 or acoustic energy reflected from the specimen 150, or both.

Audible sound waves may spread out in all directions, whereas ultrasound waves can be generally collimated and may reduce noise caused by reflectance and enhance transmission through the specimen 150. As used herein, the term "ultrasound" generally refers to, without limitation, sound with a frequency greater than about 20,000 Hz (hertz). For a given ultrasound source (e.g., an ultrasound emitter), the higher the frequency, the less the ultrasound signal may diverge. The frequency of the ultrasound signals can be increased to sufficiently collimate the signals for effective transmission through the processing media 170 and the specimen 150. To analyze a fragile specimen, relatively high frequency ultrasound can be used to minimize, limit, or substantially prevent damage to such specimen.

Additionally or alternatively, the transmitter 120 can include, without limitation, energy emitters configured to output ultrasound, radiofrequency (RF), light energy (e.g., visible light, UV light, or the like), infrared energy, radiation, mechanical energy (e.g., vibrations), thermal energy (e.g., heat), or the like. Light emitters can be light emitting diodes, lasers, or the like. Thermal energy emitters can be, without limitation, heaters (e.g., resistive heaters), cooling devices, or Peltier devices. Energy emitters can cooperate to simultaneously or concurrently deliver energy to the specimen 150 to monitor a wide range of properties (e.g., acoustic properties, thermal properties, and/or optical properties), to reduce processing times by keeping the media 170 at a desired temperature, enhance processing consistency, combinations thereof, or the like.

The receiver 130 can include, without limitation, one or more sensors configured to detect a parameter and to transmit one or more signals indicative of the detected parameter. The receiver 130 of FIGS. 1 and 2 includes at least one sensor configured to detect the acoustic energy from the transmitter 120. In other embodiments, the receiver 130 can include one or more RF sensors, optical sensors (e.g., visible light sensors, UV sensors, or the like), infrared sensors, radiation sensors, mechanical sensors (e.g., accelerometers), temperature sensors, or the like. In some embodiments, the receiver 130 includes a plurality of different types of sensors. For example, one sensor can detect acoustic energy and another sensor can detect RF energy.

The computing device 160 of FIG. 1 is communicatively coupled (e.g., electrically coupled, wirelessly coupled, capacitively coupled, inductively coupled, or the like) to the transmitter 120 and the receiver 130. The computing device 160 can include input devices (e.g., a touch pad, a touch screen, a keyboard, or the like), peripheral devices, memory, controllers, processors or processing units, combinations thereof, or the like. The computing device 160 of FIG. 1 is a computer, illustrated as a laptop computer.

Figure 3:
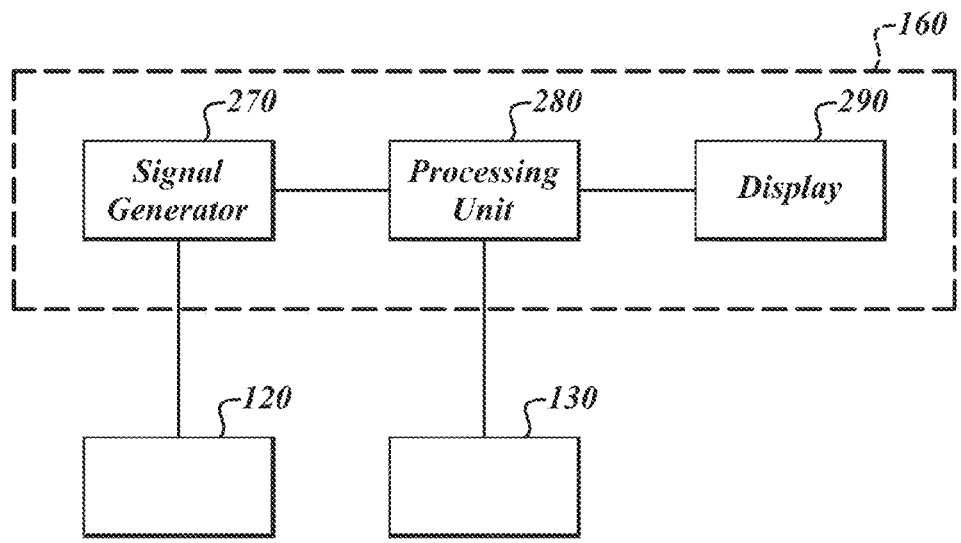
FIG. 3 is a block diagram of components of an analyzer and a computing device, in accordance with one embodiment.

FIG. 3 shows the computing device 160 (illustrated in dashed line) including a signal generator 270, a processing unit 280, and a display 290. The signal generator 270 can be programmed to output drive signals. Drive signals can have one or more sinusoidal waveforms, step waveforms, pulse waveforms, square waveforms, triangular waveforms, sawtooth waveforms, arbitrary waveforms, chirp waveforms, non-sinusoidal waveforms, ramp waveforms, burst waveforms, or combinations thereof. The waveform can be selected based on, for example, user input, stored parameters, or input from another system (e.g., a tissue preparation unit, staining unit, etc.). By way of example, the signal generator 270 can include an arbitrary function generator capable of outputting a plurality of different waveforms. In some embodiments, the signal generator 270 is an arbitrary signal generator from B&K Precision Corp. or other arbitrary signal generator.

The computing device 160 is communicatively coupled to a tissue processing unit that applies any number of substances to prepare the specimen for embedding. The computing device 160 can prepare a tissue preparation protocol that is used by the tissue processing unit. The tissue preparation protocol can include a length of processing time for a particular substance, target composition of a substance, temperature of a particular substance, combinations thereof, or the like.

The processing unit 280 can evaluate the change in the TOF of sound in the specimen 150 by, for example, comparing the acoustic waves outputted by the transmitter 120 to the acoustic waves detected by the receiver 130. This comparison can be repeated any number of times to monitor the fixation state of the specimen 150. In some embodiments, the processing unit 280 determines a first length of time it takes the acoustic waves to travel through the specimen 150. The processing unit 280 then determines a second length of time it takes a subsequently emitted acoustic wave to travel through the specimen 150. The first length of time is compared to the second length of time to determine, without limitation, a change in speed (e.g., acceleration) of the sound waves, an absolute and/or relative change in TOF, change in distance between the transmitter 120 and the receiver 130, change in temperature and/or density of the processing media 170, or combinations thereof. The processing unit 280 can use different types of analyses, including a phase shift analysis, an acoustic wave comparison analysis, or other types of numerical analyses.

To store information, the computing device 160 can also include memory. Memory can include, without limitation, volatile memory, non-volatile memory, read-only memory (ROM), random access memory (RAM), and the like. The information includes, but is not limited to, protocols, data (including databases, libraries, tables, algorithms, records, audit trails, reports, etc.), settings, or the like. Protocols include, but are not limited to, baking protocols, diffusion protocols, fixation protocols, tissue preparation protocols, staining protocols, conditioning protocols, deparaffinization protocols, dehydration protocols, calibration protocols, frequency adjustment protocols, decalcification protocols, or other types of routines. Protocols that alter or impact tissue density or sound transmission can be used to control the components of the computing device 160, components of the analyzer 114, microscope slide processing units, stainers, ovens/dryers, or the like. Data can be collected or generated by analyzing the specimen holder 110, the processing media 170, the specimen 150, or it can be inputted by the user.

The computing device 160 can evaluate different acoustic properties. Evaluation of acoustic properties can involve comparing sound speed characteristics of the specimen, comparing sound acceleration in the specimen, analyzing stored fixation information, and analyzing TOF. Analysis of the TOF may involve, without limitation, evaluating the total TOF, evaluating changes in TOF over a length of time (as discussed above), evaluating rates of change in TOF, generating TOF profiles, or the like. The stored fixation information can include, without limitation, information about sound speeds for different types of tissue, TOF of reagents, fixation rates, predicted fixation time, compensation protocols, percent cross-linking, TOF profiles, tissue compositions, tissue dimensions, algorithms, waveforms, frequencies, combinations thereof, or the like. In some embodiments, the computing device 160 evaluates at least one of the TOF, a TOF change, amplitude of the sound waves, an intensity of the sound waves, phase shifts, echoing, a temperature and/or density of the specimen 150, and a temperature and/or density of the processing media 170.

The computing device 160 can select, create, or modify fixation settings, with or without prior knowledge of specimen history, specimen fixation state, or type of tissue so as to improve the reliability and accuracy of diagnosis, especially an advanced diagnosis. Fixation settings include, without limitation, length of fixation time (e.g., minimum fixation time, maximum fixation time, ranges of fixation times), composition of the processing media, and temperature of the processing media. By way of example, if the specimen 150 has a known fixation state, an appropriate fixation protocol can be selected based, at least in part, on the known fixation state. If the specimen 150 has an unknown fixation state, the analyzer 114 is used to obtain information about the fixation state. For example, the analyzer 114 can obtain information about a specimen that is already partially or completely fixed. Protocol settings can be selected based, at least in part, on the obtained information. The protocol settings can include tissue preparation settings, fixation protocol settings, reagent protocol settings, or the like. In some embodiments, reagent protocol settings (e.g., types of IHC/ISH stains, staining times, etc.) can then be selected to match/compensate for the fixation state based, at least in part, on information from the analyzer 114. The analyzer 114 can thus analyze unfixed, partially fixed, or completely fixed specimens.

To process multiple tissue samples, the processing system 100 can dynamically update fixation settings. Fixation settings can be generated by analyzing the illustrated specimen 150. Another specimen taken from the same biological tissue as the specimen 150 can be processed using the new fixation settings. In this manner, the fixation process can be dynamically updated.

Figure 4:
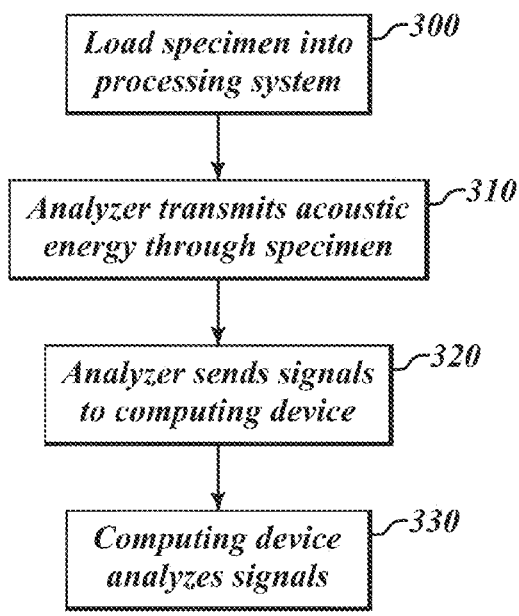
FIG. 4 is a flow diagram of an exemplary method of processing a specimen, in accordance with one embodiment.

FIG. 4 shows an exemplary method of fixing the specimen 150 to protect the specimen 150 from, for example, putrefaction, autolysis, or the like. In general, the specimen 150 can be loaded into the processing system 100. The processing media 170 contacts and begins to fix the specimen 150. The analyzer 114 monitors the fixation process. After the specimen 150 is sufficiently fixed, the specimen 150 is taken out of the fixation media 170 to conveniently avoid under-fixation and over-fixation. Details of this fixation process are discussed below.

At step 300 of FIG. 4, the specimen 150 is loaded into the specimen holder 110. To open the specimen holder 110, the plates 220, 230 can be separated. The plates 220, 230 can be coupled together to loosely hold the specimen 150. In some embodiments, the specimen holder can be a standard Cellsafe™ tissue cassette for biopsy samples from Cellpath Ltd or other types compatible with acoustic transmission. The closed specimen holder 110 is manually or automatically lowered into the container 140 and held in a docking station 312 (see FIGS. 1 and 2). The docking station 312 can be a clamp, a gripping mechanism, or other component suitable for retaining the specimen holder 110.

The processing media 170 begins to diffuse through the specimen 150 to begin the fixation process. The fixation processes may involve limiting or arresting putrefaction, limiting or arresting autolysis, stabilizing proteins, and otherwise protecting or preserving tissue characteristics, cell structure, tissue morphology, or the like. The fixative can include, without limitation, aldehydes, oxidizing agents, picrates, alcohols, or mercurials, or other substance capable of preserving biological tissues or cells. In some embodiments, the fixative is NBF. In some fixation processes, the media 170 is a fixative that causes cross-linking of the specimen 150. Some fixatives may not cause cross-linking.

At 310, the analyzer 114 transmits acoustic energy through the specimen 150. The signal generator 270 (see FIG. 3) can output a drive signal to the transmitter 120 which, in turn, emits acoustic energy that is ultimately transmitted through the specimen 150.

At 320, the receiver 130 detects the acoustic energy and outputs receiver signals to the computing device 160 based on the detected acoustic energy. The receiver signals may or may not be processed (e.g., amplified, modulated, or the like).

At 330, the computing device 160 analyzes the receiver signals. The computing device 160 can control the processing system 100 to enhance processing reliability, reduce processing times, improve processing quality, or the like. For example, the temperature of the processing media 170 of FIG. 2 can be controlled to enhance diffusion of the media 170 to reduce processing times, control cross-linking, etc.

Once the tissue sample 150 reaches a desired fixation state, the specimen holder 110 is removed (e.g., manually or automatically) from the media bath. The fixed specimen 150 can be embedded, sectioned, and stained without performing tests that cause specimen waste.

The processing system 100 of FIGS. 1 and 2 can include any number of thermal devices, mechanical devices, sensors, or pumps. The mechanical devices can include, without limitation, agitators (e.g., fluid agitators), mixing devices, vibrators, or the like. The sensors can be, without limitation, acoustic sensors, motion sensors, chemical sensors, temperature sensors, viscosity sensors, optical sensors, flow sensors, position sensors, pressure sensors, or other types of sensors. The sensors can be positioned at various locations about the chamber 180.

TOF measurements can be used to monitor preparation processes, including delivery processes, fixation processes, etc. Theoretical changes in TOF can be calculated based on the distances between components in the processing system 100, the dimensions of the specimen 150, a length of a sound path 313 (see FIG. 2) along which the acoustic energy travels, and the acoustic properties of the fixative media 170 and specimen holder 110. The computing device 160 can analyze calculated values to determine fixation settings, such as initial fixation settings.

Table 2 below shows calculated theoretical changes in TOF based on the speed of sound in water (1,482 m/s), the speed of sound in unfixed muscular tissue (1,580 m/s), and the speed of sound in fixed muscular tissue (1,600 m/s). The theoretical calculations can be compared to measured values in order to modify the fixation process. In some embodiments, the theoretical calculations are used to determine initial settings for the fixation process. The initial settings may include waveforms, amplitude of acoustic energy, frequency of acoustic energy, processing temperatures, or the like.

TABLE 2

| Sound path | Dimension | Distance [mm] | TOF [us] | TOF after fixation [us] |
|---|---|---|---|---|
| transmitter->cassette/specimen | D1 | 20 | 29.6 | |
| specimen | D2 | 4 | 6.32 | 6.4 |
| specimen -> specimen holder | D3 | 1 | 1.48 | |
| Specimen holder ->receiver | D4 | 25 | 37 | |
| TOTALS | | 50 | 74.4 | 74.48 |
| | | | delta [ns] | 80 |

FIG. 2 shows the distance $D_1$ from the transmitter 120 to the specimen 150, the distance $D_2$ between opposing surfaces of the specimen 150, the distance $D_3$ from the specimen 150 to the outer surface of the second plate 230, and the distance $D_4$ from the specimen holder 110 to the receiver 130. The sound speeds and densities of common tissue types are well known in the art. These known values can be used to calculate the change in TOF and determine initial fixation settings. Because sound speeds are dependent on the temperature of the medium and the distance of the measurement channel may be dependent on thermal expansion coefficients of the related components, a reference TOF measurement of the medium and the measurement channel at a given temperature of the medium and the test environment may be performed in some embodiments. This reference measurement may be used to compensate for the TOF measurements of the specimen.

The total TOF can be determined by the individual travel times of the sound waves traveling first through a portion of the media 170 for the time "t1" across the distance $D_1$, followed by the time "t2" as the sound waves travel across the distance $D_2$, and finally the time "t3" as the sound waves travel the remaining distances $D_3$ and $D_4$. Thus, the total TOF=t1+t2+t3. Changes in the total TOF can be measured and related to the state of fixation and thus relate primarily or only to the time "t2." The information of an unimpeded sound path (e.g., a sound path without a sample insertion as a reference) may be used to identify variation of the total TOF due to, for example, changes of the media 170 (e.g., temperature changes, density changes, etc.).

Figure 5:
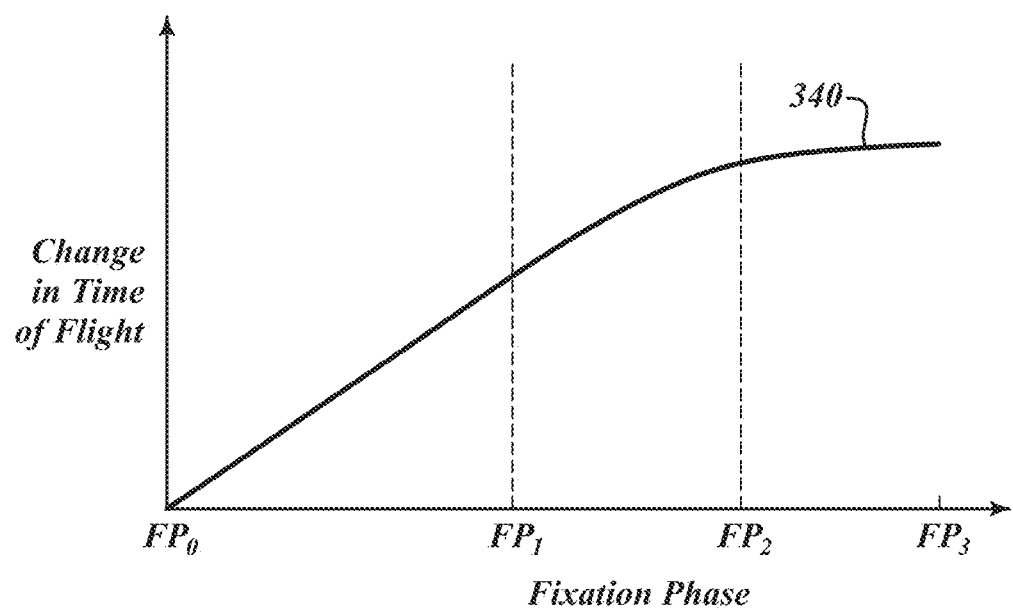
FIG. 5 is a graph of fixation phase versus change in time of flight.

Different types of tissue can have different acoustic characteristics. FIG. 5 is a non-limiting exemplary graph of fixation phase versus change in a TOF. A curve 340 can be generated by analyzing a specimen. Different types of tissue may generate different types of curves, as discussed below in connection with FIGS. 30-38. The computing device 160 can correlate the different curves to different tissue types. To process a fresh specimen, a curve can be selected corresponding to the same or similar tissue type as the fresh specimen. The computing device 160 can provide an appropriate processing protocol based on the curve. The protocol can include, without limitation, a reagent delivery protocol, fixating protocol, a tissue preparation protocol, an embedding protocol, a decalcification protocol, a staining protocol, or combinations thereof. Information can also be obtained while the protocol is performed to modify the protocol or select another protocol. By way of example, the curve 340 can be used to determine, at least in part, when to remove a specimen from a fixation media.

Curve fitting techniques using polynomials, trigonometric functions, logarithmic functions, exponential functions, interpolations (e.g., spline interpolations) and combinations thereof can be used to generate the curve 340 which approximates collected data. Some non-limiting exemplary curve fitting techniques are discussed in connection with FIGS. 13-16.

At an initial fixation phase FP° in FIG. 5, the unfixed specimen 150 is exposed to the processing media 170. It is believed that the outermost portions of the specimen 150 may begin to cross-link and the media 170 can diffuse into the specimen 150. As the fixation phase increases from FP° to $FP_1$, the change in TOF gradually increases with respect to the fixation phase. From $FP_1$ to $FP_2$, the cross-linking approaches the interior regions of the specimen 150. The change in TOF is nonlinear with respect to the fixation phase. As the fixation phase approaches $FP_2$, the rate of change of the TOF change begins to rapidly decrease. From $FP_2$ to $FP_3$, the specimen 150 becomes saturated until there may be over-saturation at about $FP_3$. Approaching $FP_3$, the slope of the curve 340 continues to decrease as it approaches zero, corresponding to when the specimen 150 may be at risk of over-fixation. The fixation process can be controlled based on, for example, the slope of the curve 340, a minimum TOF change, a maximum TOF change, combinations thereof, or the like.

A predictive algorithm can be used to determine a desired processing time to achieve a desired level of fixation. The computing system 160 can store and select predictive algorithms based on the desired amount of infusion, cross-linking, etc. If the fixation media 170 diffuses at a non-linear rate, a non-linear diffusion predictive algorithm can be selected. If the fixation media 170 causes cross-linking at a non-linear rate, a non-linear fixation predictive algorithm can be selected. For example, cross-linking could exhibit exponential decay so an exponential decay curve can be used to estimate an end of processing time. The desired level of cross-linking can be selected based on the tissue type, the analysis to be performed, the expected storage time, or other criteria known in the art. For example, the predictive curve can be used to determine a predicted stopping time for which cross-linking should be about 99% complete.

A Levenberg-Marquardt algorithm or other type of non-linear algorithm can be used to generate an appropriate best fit curve. In some predictive protocols, the Levenberg-Marquardt algorithm uses an initial value to generate a curve. A damping-undamping scheme can produce the next iteration. Non-limiting exemplary damping-undamping schemes are described in the paper "Damping-Undamping Strategies for the Levenberg-Marquardt Nonlinear Least-Squares Method" by Michael Lampton. The closer to the actual curve of the initial value, the more likely it is that the algorithm will provide the desired best-fit curve. In some protocols, a plurality of values in the data set (e.g., a first value, a middle value, and a last value) are used to produce an exponential curve that fits the three values. The initial values can be selected based on known values for similar tissue samples. After performing the iterative process, a best fit curve is generated. The best-fit curve can be used to determine the predicted state of the specimen at different times during processing. This can be helpful to develop a schedule to increase processing throughput, especially if the processing system allows for individual processing, as discussed in connection with FIG. 21.

Figure 6:
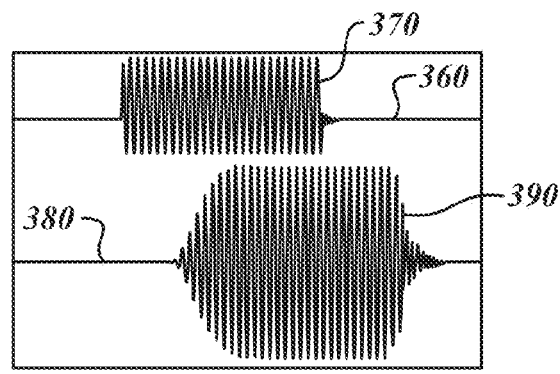
FIG. 6 is a plot showing a timing relationship between an outputted signal and a received signal.

FIG. 6 shows a timing relationship between a signal 360 from the transmitter 120 and a detected signal 380. The signal 360 can have a sufficient number of signal bursts to evaluate phase changes of waves entering and exiting the specimen 150 at a particular distance. By way of example, acoustic waves 370 of the signal 360 are illustrated as a pulse burst and can be a 1 MHz sine burst with 53 cycles, 5.3 ms repetition rate, and a 7.4 V amplitude. Other acoustic waves with different pulse bursts, numbers of cycles, repetition rates, amplitudes, etc. can also be used. The detected signal 380 corresponds to the signal received by the receiver 130. A pulse burst 390 corresponds to the signal burst 370.

Figure 7:
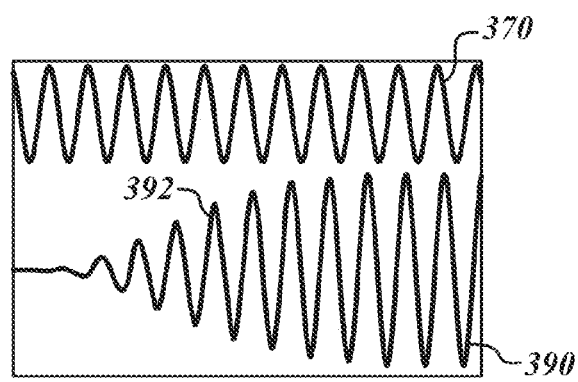
FIG. 7 is an enlarged view of a portion of the outputted signal and a portion of the received signal.
Figure 8:
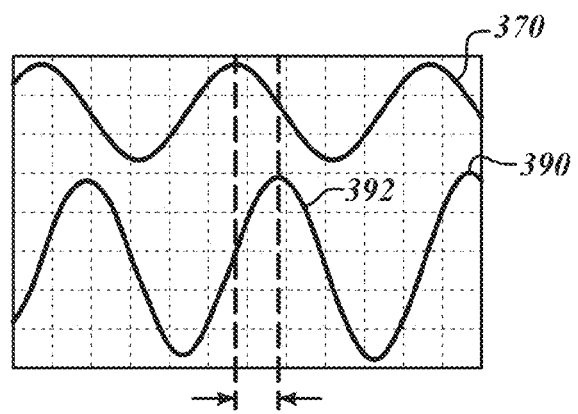
FIG. 8 is a detailed view of a portion of the outputted signal and a corresponding portion of the received signal.

FIGS. 7 and 8 show the relationship between the signal burst 370 and the received acoustic waves 390. A change in TOF, if any, can be determined based on a comparison of the waves 370, 390. If the TOF does not change, there will be no phase shift between the waves 370, 390 over time. If there is a TOF change, there will be a phase shift over time. For example, at the fifth wave 392, there is about 38.28 µs phase delay or shift, measured against the reference signal 370. As a sample undergoes fixation, the sound speed in most types of tissue (e.g., muscle tissues, connective tissues, etc.) typically increases. However, some fatty tissues will cause a decrease of sound speed during fixation. The system 100 can detect a relative phase angle difference resulting from a phase shift caused by an early or late arrival of the pulse packet 390. A large number of acquisitions can be obtained. For example, about 100 to about 1,000 phase comparisons can be performed at a rate of about 70 times per second. In one embodiment, the scheme can monitor target changes of at least 125 ns at a frequency of about, for example, 4 MHz.

FIG. 9 shows the relationship of outputted waves 393, received waves 394, and a comparison curve 391. The comparison curve 391 shows phase differences, illustrated as an analog voltage output, that reflect an integrated phase difference accumulated from a comparison (e.g., a synchronous comparison) of two wave packets 395, 397. The integrated phase difference can be used to determine when to evaluate a phase difference between the two waves 393, 394 or what part of the waves 393, 394 to compare.

A trigger point, indicated by a dashed line 398, can be communicated to the computing device (e.g., a data capture system). The trigger point 398 can be selected based on a settling point, rate of change, or the like of the curve 394. An electronic data capture system of the system 160 can analyze the waves 393, 394 at the trigger point and can have a resolution around 1 ns or better (based on +/−1 sd at n=7 captured pulse packets) in shadowed transmission mode. Any number of trigger points can be selected along the curve 391 based on the desired amount of sampling.

Figure 10A:
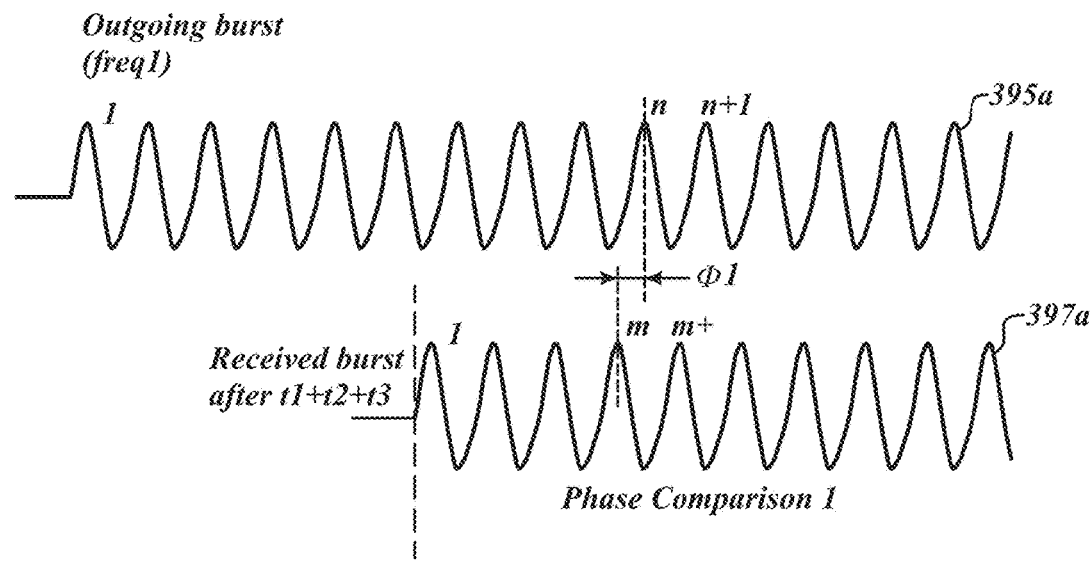
FIG. 10A is a plot showing a timing relationship between an outputted signal and a received signal, in accordance with one embodiment.
Figure 10B:
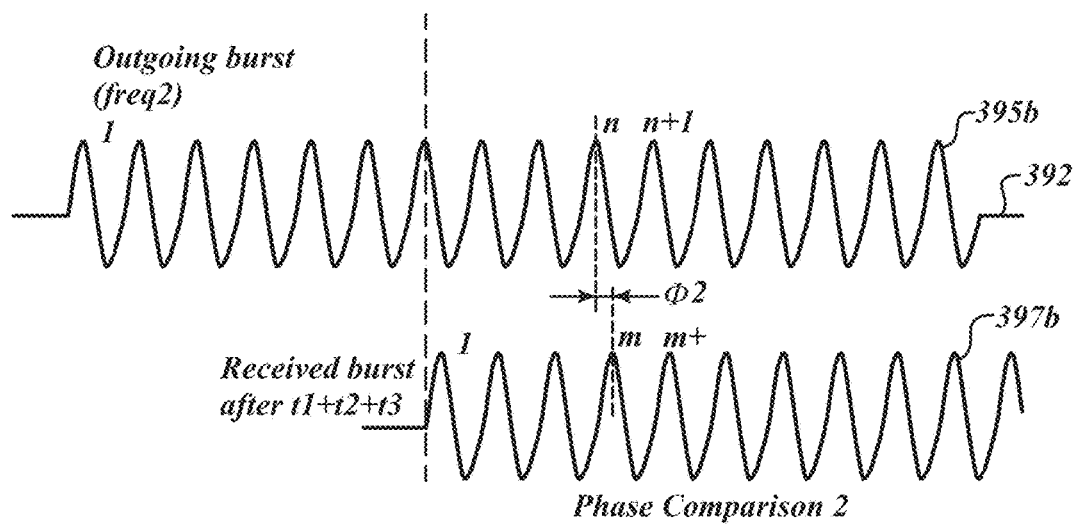
FIG. 10B is a plot showing a timing relationship between an outputted signal and a received signal, in accordance with yet another embodiment.

FIGS. 10A and 10B show phase angle relationships based on the frequency of outgoing waves. In FIG. 10A, an outgoing burst signal 395a, a received burst signal 397a, and an initial phase relationship Ø1 caused by the signal 397a traveling through the sample 150. FIG. 10B shows an outgoing burst wave 395b outputted at a frequency 2 higher than the frequency 1 of wave 395a of FIG. 10A. The outgoing wave 395b of FIG. 10B has a reduced wavelength as compared to the outputted wave 395a. As such, the phase relationship Ø1 is different from the phase relationship Ø2. Because the TOF is primarily or only dependent on the distance of travel and the density of the media or sample, the phase relationship can be freely configured by selecting the frequency (or other characteristics) of the outgoing waves. Accordingly, the computing system 160 can select the frequency of the outgoing wave based on a desired phase relationship.

Frequencies and the resulting phase relationships can be correlated to determine how changes of the outgoing frequency will result in phase relationship changes, which in turn can be used to monitor the sample 150. A monitoring protocol can include, without limitation, outputting a plurality of waves with different frequencies to generate a plurality of phase relationships. A comparison (e.g., an extended phase range comparison) can be accomplished by adaptively monitoring phase angle progression. Outgoing frequencies can be changed (e.g., incrementally changed) by the signal generator 270 to keep the phase relationship in the favorable range. The phase angle change is linearly dependent on the frequency change and therefore can be added successively as an absolute TOF increment to any additional changes observed by the phase comparison itself. Because most reactions being monitored are in a time range of several tens of minutes, an adaptive frequency change can be easily achieved.

Figure 11:
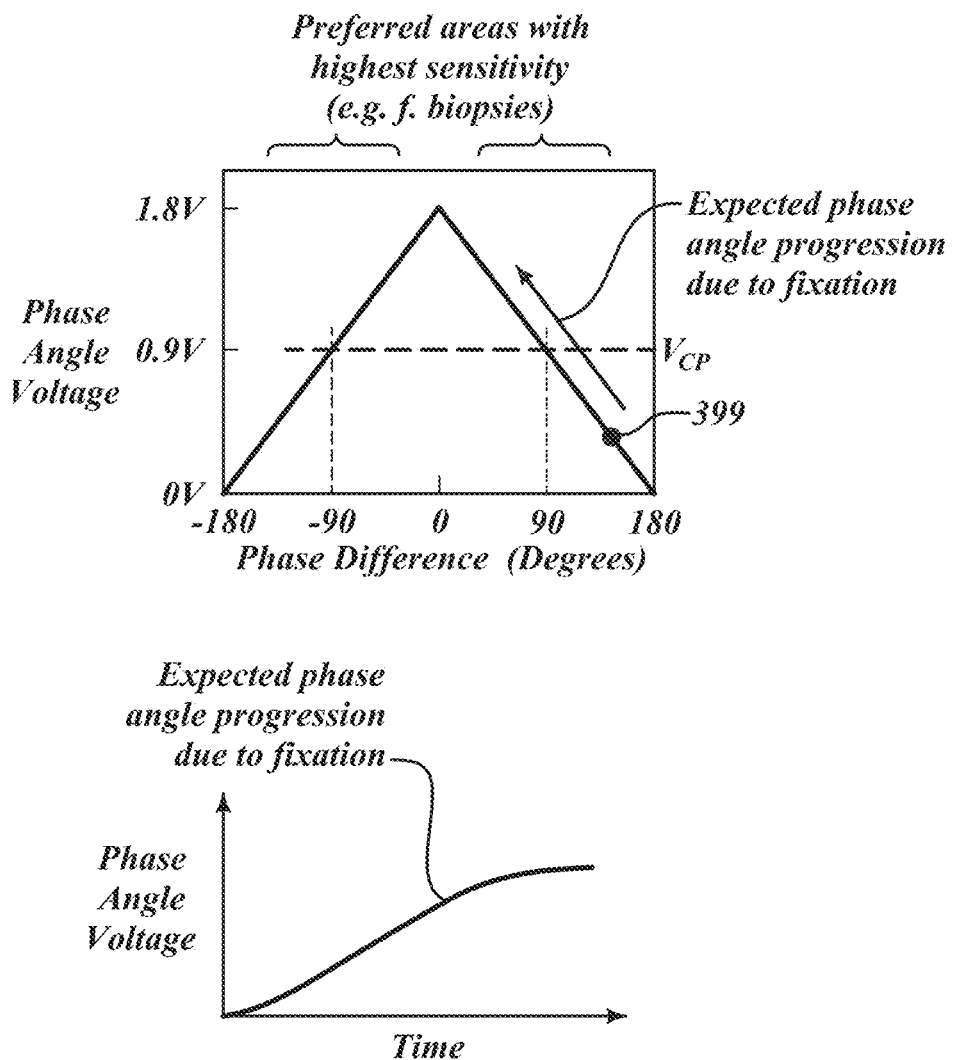
FIG. 11 is a graph of phase difference versus phase angle voltage and a plot showing time versus phase angle voltage with an expected phase equal progression due to fixation.

The base wavelength for an ultrasound transducer may result in a phase detection limit. For example, the ultrasound transducer 120 may output a signal at a frequency of about 4 MHz, 0-180 degrees, at about the 125 ns range. Different ultrasound receivers may provide a larger phase angle range, but depth resolution for the target thickness may be limited to thicker samples. For greater phase angle differences (e.g., greater than 180 degrees), the integrated voltage can be reversed in polarity, or repeat itself for phase angle differences greater than 360 degrees. Because monitoring of fixation may rely on relative phase angle changes, the initial phase angle can be optimized on a target, such as by varying the base wavelength in the arbitrary function generator 170 to establish an initial setting with a favorable phase relationship, for example, the point 399 in the graph of FIG. 11. FIG. 11 also shows phase differences that provide high sensitivity. Other methods may not rely on phase comparison measurements and instead utilize chirped pulse excitation and correlation or convolution methods to calculate absolute TOF with similar precision and resolution.

A wide range of compensation techniques can be utilized to analyze TOF measurements. One compensation technique for relatively large phase shifts during TOF monitoring relies on reduction principles. A mathematical reduction principle can use, for example, multiple discrete excitation frequencies (=wavelength scans) sent in succession of bursts at the same target location. A change in time, $\Delta T$, can represent the actual time delay between when a wave is sent and when the wave is received. A plurality of waves of different wavelengths, $\lambda_1, \lambda_2, \ldots, \lambda_n$, can be emitted.

The received waves can be compared with the outgoing waves to determine corresponding phase changes, $\Delta\theta_{\lambda_1}$, $\Delta\theta_{\lambda_2}, \ldots \Delta\theta_{\lambda_n}$. The computing device 160 can narrow down the actual value of $\Delta T$ to a subset of values which is much smaller than the set of all possible values for $\Delta T$. If there is a range of wavelength scans, $\lambda_1, \lambda_2, \ldots, \lambda_n$, and their corresponding phase changes, $\Delta\theta_{\lambda_1}, \Delta\theta_{\lambda_2}, \ldots \Delta\theta_{\lambda_n}$, the computing device 160 can use each reading to further narrow down an estimated until there is only one feasible value $\Delta T$, which can correspond to the absolute time-of-flight. Phase detection can be performed using a demodulator and a controller to provide high resolution. For example, sub-nanosecond resolution at a total TOF of about 20 μs can be achieved with a microcontroller (e.g., an 8-bit microcontroller) and a demodulator chip).

Figure 11A:
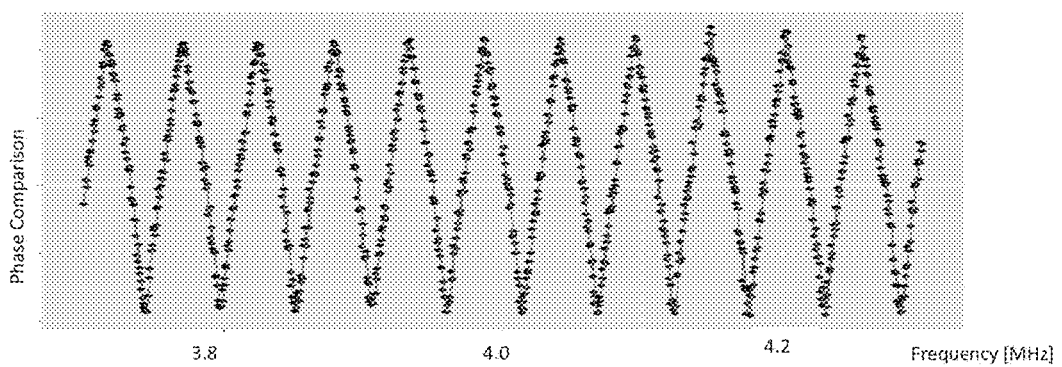
FIG. 11A is a plot of frequency versus phase comparison in accordance with one embodiment.

FIG. 11A is a plot of frequency versus phase comparison in accordance with one embodiment. A programmable function generator can generate many sine waves at different frequencies. By measuring the phase difference at each frequency, we can reconstruct the actual time-of-flight. A comparison can be performed as a function of frequency to unique time of flights. As shown in FIG. 11A, the comparison wave can be a generally triangle wave with a slope corresponding to the time-of-flight. TOF can also be determined based on techniques disclosed in U.S. application Ser. No. 13/372,040, filed on Feb. 13, 2012, and incorporated by reference in its entirety.

The change in phase $\Delta\theta_\lambda$ can be measured at a given frequency, $\lambda$. Because there may be many values for $\Delta T$ that would yield the same $\Delta\theta_2$, the $\Delta T$ can be estimated or predicted based, at least in part, on a specific $\Delta\theta_\lambda$ since most values for $\Delta T$ would not yield a given $\Delta\theta_\lambda$ (the true value of $\Delta T$ satisfies the equation $\Delta T = N/(2\lambda) + \Delta\theta_\lambda$ for some integer N). A program can be used to at least narrow down the true value of $\Delta T$ to a subset of values which is much smaller than the set of all possible values for $\Delta T$ based on an estimated $\Delta T$ from a specific $\Delta\theta_\lambda$. The computing device 160 can generate a range of wavelength scans, $\lambda_1, \lambda_2, \ldots, \lambda_n$, and their corresponding phase changes, $\Delta\theta_{\lambda_1}, \Delta\theta_{\lambda_2}, \ldots \Delta\theta_{\lambda_n}$ as detailed above.

An interactive algorithm can be used to determine $\Delta T$ and can be used to minimize or avoid problems associated with solving for $\Delta T$ algebraically (e.g., problems attributable to the noisy nature of TOF measurements). In some interactive algorithms, a $\Delta T$ is estimated or predicted. A theoretical $\Delta\theta_\lambda$ can be determined for that $\Delta T$ and can be compared to measured $\Delta\theta_\lambda$'s to assign a penalty function. The penalty function can be the sum of the squared differences between the theoretical $\Delta\theta_\lambda$'s and the measured $\Delta\theta_\lambda$'s. The true value of $\Delta T$ can be the minimizer of the penalty function. The method for minimizing this function can be determined using different techniques, such as a sweep of values or a binary search. Additionally or alternatively, a gradient descent, Newton method (including Gauss-Newton algorithm), or Levenberg-Marquardt method could be used. Other algorithms can also be utilized, if needed or desired. In some protocols, one or more out-of-range values (e.g., values <0.2 and/or values >1.5) can be discarded. The out-of-range values can be selected based on criteria corresponding to characteristics of the tissue sample.

A phase detection algorithm can be used to compare an outgoing wave with a corresponding received wave. One type of phase detection algorithm is a range extension algorithm involving multiple wavelengths of phase angle changes for acoustic speed measurements. When the speed of acoustic waves changes significantly, the computing device 160 may base wave comparisons on a different period of the wave than it started on, resulting in a sudden change from an increasing TOF to a decreasing TOF or resulting in a sudden change from a decreasing TOF to an increasing TOF. The sudden change is attributable to the comparison of different phases, thereby leading to artificial data. Rate of changes in TOF can be evaluated to determine whether the TOF changes are artificial changes due to such out of phase comparisons. For example, the second derivative of the TOF curve can be used to determine whether a local maximum TOF or a local minimum in TOF is a natural change in TOF or an artificial change in TOF.

Figure 12:
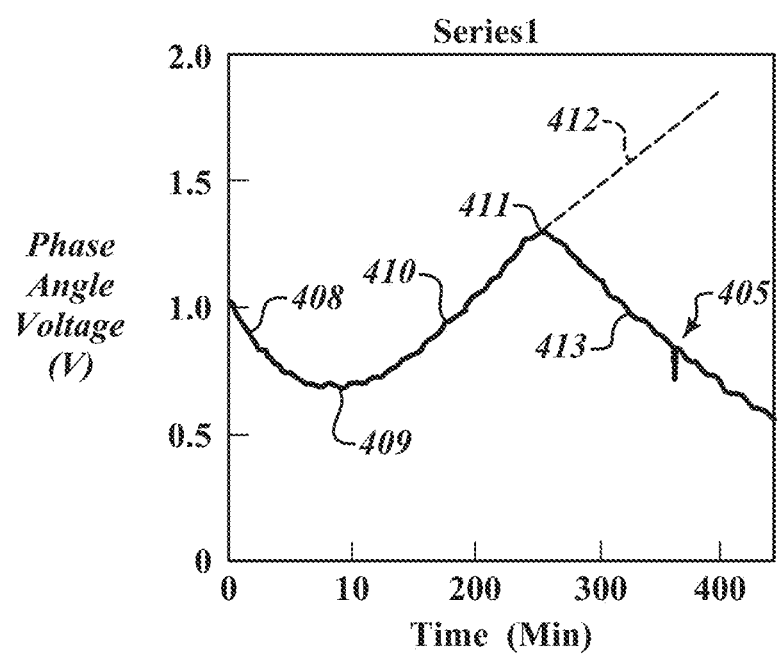
FIG. 12 is a plot of fixation time versus phase angle voltage.

FIG. 12 shows a graph of time versus TOF signal. A curve 405 gradually decreases at 408 to a local minimum 409. The curve 405 then increases at 410 to an artificial local maximum 411. The actual TOF continues to gradually increase, as indicated by the dashed curve 412. The peak 411 is generated based on an out of phase comparison. The curve 405 at 413 continues to decrease at time greater than 260 based on the out of phase comparison. As shown in FIG. 12, there is a significant difference between the actual TOF 412 and the artificial TOF 413.

Figure 13:
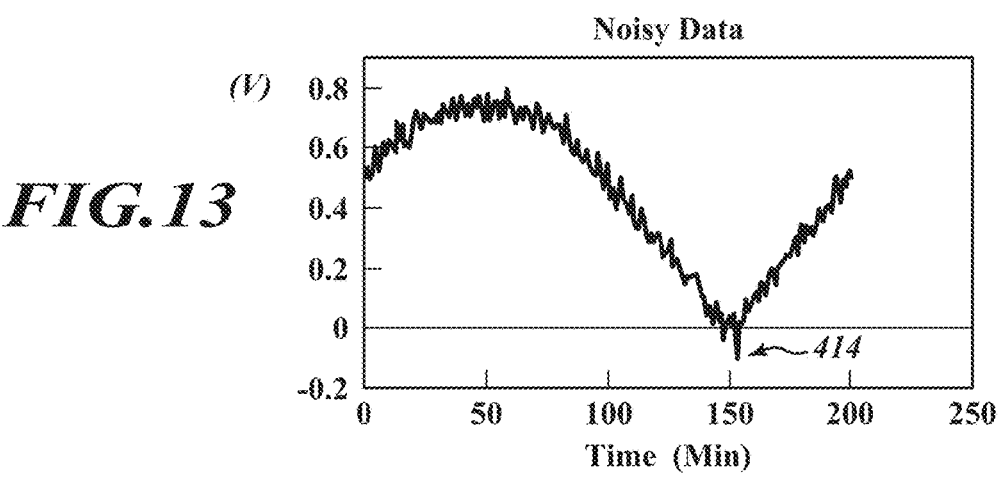
FIG. 13 is a plot of fixation time versus phase angle voltage.

Artificial measurements can be identified to avoid the peak 411. By way of example, FIG. 13 is a graph of time versus TOF with noisy data. The TOF increases from a time=0 minutes to about t=55 minutes. The TOF gradually decreases from 55 minutes to about 150 minutes. The TOF suddenly begins to increase at about 150 minutes. A program can determine whether the sudden change in TOF is accurate or artificial.

Figure 14:
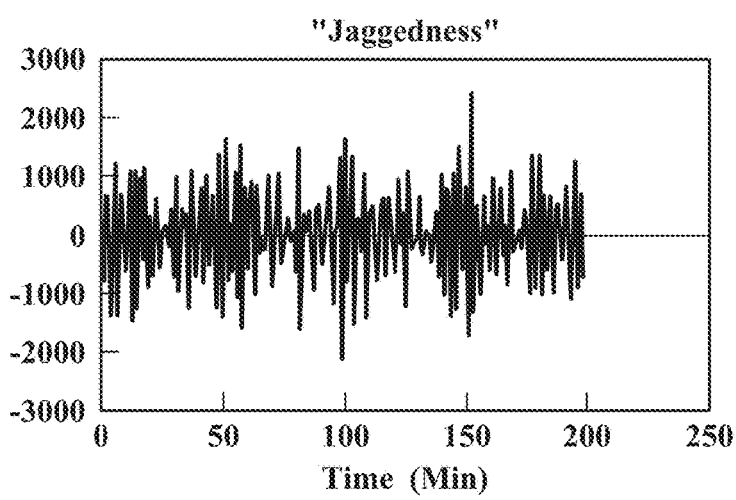
FIG. 14 is a plot showing jaggedness of the data of FIG. 13.

FIG. 14 shows a plot generated using numerical differentiation (e.g., finite-difference methods) of the data of FIG. 13 which increase the signal-to-noise ratio resulting in jaggedness curve 414 that is not suitable for determining whether changes in TOF are natural or artificial. The spike at time of about 155 corresponds to artificial changes from a decreasing TOF to an increasing TOF based on a comparison between difference phases of waves. Based on the numerous large spikes in FIG. 14, it may be difficult to accurately determine whether a spike corresponds to an artificial or a natural change in TOF.

Figure 15:
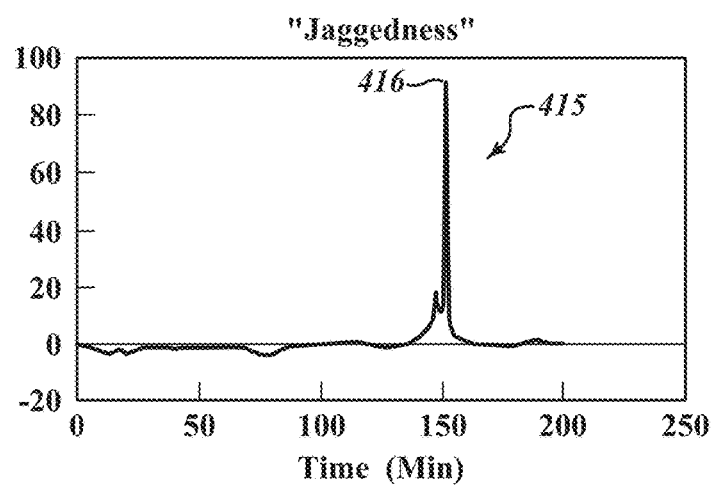
FIG. 15 is a plot of jaggedness generated using a smoothing algorithm and the data of FIG. 13.

FIG. 15 shows jaggedness of the noisy two-peak curve of FIG. 13 using a smoothing algorithm, such as a total variation smoother algorithm. The total variation smoothing algorithm can be used to smooth the raw data of FIG. 13 before generating the jaggedness plot. A compensation program can recognize that the change in time of flight at about t=150 is artificial and recompare different phases of the waves to ensure that the general trend of the time of flight as t approaches 150 is generally maintained. The large spike 416 at 150 minutes can be conveniently identified in FIG. 15, while the natural peak is barely identifiable. A compensation program can be used to compensate for the spike 416. Such compensation programs can include, without limitation, an algebraic algorithm or other type of compensation algorithm.

Figure 16:
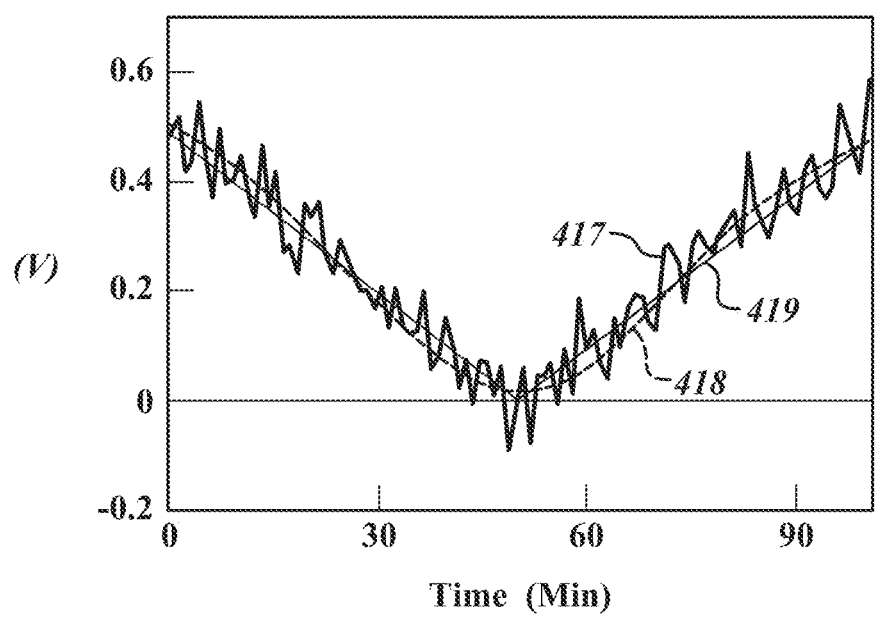
FIG. 16 is a plot of curves generated using different algorithms for analyzing noisy data.

Noise can be reduced without eliminating desired data. One noise-reducing method that does not over-smooth data (e.g., cusps) is discussed in "Numerical Differentiation of Noisy, Nonsmooth Data" by Rick Chartrand, published by Los Alamos National Laboratory, Dec. 13, 2005. The method is an example of a total variation smoother which smoothes noise while preserving true cusps, thereby minimizing, eliminating, or limiting only unwanted noise. FIG. 16 shows a data plot 417, a first smoothed curve 418 (shown in dashed line), and a second smoothed curve 419. Numerous cusps of the data plot 417 are eliminated in the first smoothed curve 418 which was generated using a numerical differentiation algorithm designed to remove sharp peaks/valleys. The second curve 419 was generated using total variation smoother algorithm which preserves true cusps. Thus, the second curve 419 is well suited for identifying inaccurate (e.g., artificial peaks/valleys) TOF signals at the time of 49 minutes as compared to the first smoothed curve 418.

Movement of tissue within a specimen holder can lead to inaccurate measurements. If the tissue sample 150 moves inside the specimen holder 110, the change in position of the specimen can significantly alter measurements for monitoring cross-linking, changes in specimen density, or the like. Averaging, comparing, or otherwise analyzing data obtained from one or more analyzers, as discussed in connection with FIG. 18, can be used to compensate for such movement. The computing device 160, for example, can include different types of algorithms that use data obtained for a plurality of analyzers. If tissue shifts within the specimen holder (e.g., when a cassette is jarred or a cassette moves rapidly through media), movement of the tissue relative to the cassette can be accounted for to avoid changes attributable to tissue migration.

Tissue analyzers described herein can also analyze tissue samples after fixation. For example, the tissue analyzer 114 of FIGS. 1 and 2, or a modified tissue analyzer, can obtain information about a tissue sample embedded in a material, a cut mountable section (e.g., a cut strip of embedded tissue), or the like. Information about the specimen can thus be obtained before fixation/processing, during fixation/processing, and after fixation/processing. Specimens can be analyzed any number of times throughout processing to ensure that the specimen is properly prepared for examination. One method of analyzing fixed tissue is described below with respect to an embedded specimen.

In some embodiments, the specimen 150 is a block of embedding material containing a tissue sample. The embedding material can have mechanical properties that may facilitate sectioning. Materials for embedding include, but are not limited to, paraffin, resin (e.g., plastic resins), polymers, agarose, nitrocellulose, gelatin, mixtures thereof, or the like. Paraffin is a white or generally colorless water insoluble solid substance that is resistant to many reagents. Paraffin can be a mixture of hydrocarbons chiefly of the alkaline series obtained from petroleum. A wide range of different mixtures of similar hydrocarbons can be used to make paraffin, and these mixtures can be solid, semi-solid, and/or oily. The acoustic properties of these types of embedding materials may be known or may be determined using the analyzer 114. The speed of sound traveling through the block (including the tissue) can be analyzed to select an appropriate protocol to be performed on the tissue sample. A wide range of different variables (e.g., dimensions of the block, degree of fixation of the tissue, temperature of the block, temperature of the tissue, etc.) can affect the speed of sound. Although the density of the embedding material may impact sound speeds, TOF measurements may yield important information about tissue properties, tissue fixation state, the impregnating process used to embed the tissue, or the like. The contribution to the sound speed by the tissue can be isolated out from the contribution to the sound speed of the embedding material to evaluate the properties of the tissue.

After analysis, the embedded specimen can be cut into mountable sections, placed on a microscope slide, and then dried. A microtome can cut the specimen into thin mountable sections, for example, slices on the order of about 5 microns to about 6 microns thick. Each section can include a portion of the tissue sample and some of the embedding material. Different techniques can be used to transfer the tissue samples onto the microscope slide. In some embodiments, the cut sections are floated on water to spread or flatten the sections. If the sections are pieces of paraffin embedded tissue, the sections can be floated on a warm bath to keep the sections in generally flat configurations, thereby reducing or preventing folding, creasing, or bending. A microscope slide is inserted into the warm bath. A front surface of the slide is used to pick up the tissue samples.

Reagents can be applied to the tissue samples. The composition of the reagent, processing times, or volume of reagent can be selected based on the information obtained by the processing system 100. Staining protocols for the embedded tissue samples can be selected with limited or substantially no known information about the tissue sample 150. Even archived tissue samples can be matched with suitable reagents. Reagents include, without limitation, stains, wetting agents, probes, antibodies (e.g., monoclonal antibodies, polyclonal antibodies, etc.), antigen recovering fluids (e.g., aqueous- or non-aqueous based antigen retrieval solutions, antigen recovering buffers, etc.), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast.

The analyzer 114 can be used to determine whether the specimen 150 has been fixed and, if so, the degree of fixation. If the specimen 150 has not been fixed, the specimen 150 can be fixed. If the specimen 150 is properly fixed, the specimen 150 can be removed from the fixative bath or the fixative can be deactivated. Deactivation of the fixative 170 can be achieved by diluting the fixative, exchanging fluids, rendering the fixative inactive, or the like.

If the specimen 150 has been left in the fixative 170 for an extended period of time, it may be over-fixed. Specimens are often inadvertently left in fixatives, for example, overnight. In such cases, the specimen may not need any additional fixing. The analyzer 114 can analyze the characteristic sound speeds of the specimen 150 and compare the measured characteristic sound speed to a typical sound speed for the tissue type of the specimen 150. Based on the comparison, the computing device 160 can determine the degree of fixation, if any, of the specimen 150. For example, if the sound speed does not change a threshold amount within an expected time frame, the specimen 150 is already fixed. Thus, the specimen 150 can be removed from the fixation bath or the fixation process can be stopped to avoid over-fixation. By way of another example, the measured characteristics can be compared to stored values (e.g., sound speed characteristics of fixed tissue) to determine the degree of fixation. If the specimen 150 is already fixed, the characteristic sound speed will correspond to the sound speed of fixed tissue.

Figure 17:
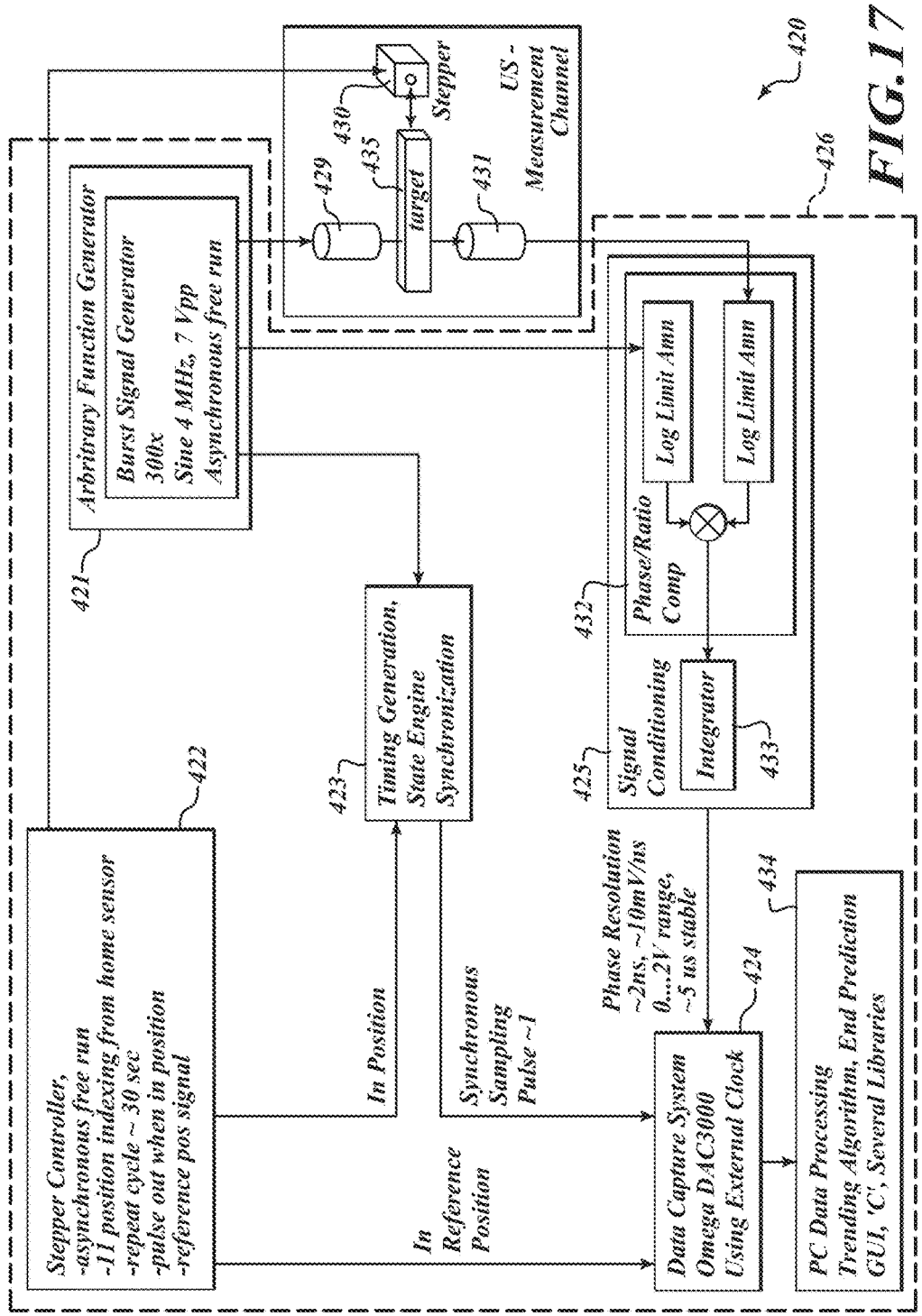
FIG. 17 is a block diagram of a processing system, in accordance with one embodiment.

FIG. 17 shows a processing system 420 with a computing device 426 configured to perform signal comparison by, for example, capturing and analyzing ultrasound phase velocity changes. The computing device 426 can monitor perfusion, thermal equilibration, alcohol contraction, evaporation, fixation, combinations thereof, or the like. The computing device 420 is similar to the computing device 160 discussed in connection with FIG. 3, except as detailed below.

A function generator 421 can send signals to a synchronization device 423 and to a transmitter 429. A controller 422 sends signals to the synchronization device 423 and to a positioning mechanism 430. The positioning mechanism 430 positions a sample between the transmitter 429 and a receiver 431 based, at least in part, on the signals from the controller 422.

The synchronization device 423 can synchronize signals based on phase shifts, outputted/received frequencies, signal comparisons, or the like and outputs signals to a capture system 424. The capture system 424 can be a data capture system the relies on an internal or external clock. In some embodiments, the capture system 424 can be an Omega DAC 3000 sold by Omega Engineering, Inc. or similar type of device. Other types of capture systems can also be utilized, if needed or desired.

A signal conditioner 425 receives output from the function generator 421 and output from the receiver 431. An analog or digital phase/ratio comparator 432 outputs signals to an integrator 433 (e.g., a digital integrator, an analog integrator, etc.), which in turn outputs signals to the capture system 424. The signal conditioner 425 can include other components, circuits, signal processing units such as DSPs, FPGAs, digital-to-analog devices, analog-to-digital devices, amplifiers (e.g., gain amplifiers), RF/IF gain phase detectors, or the like.

A computing unit 434 receives signals from the capture system 424 and can include frequency/phase shift databases for correlating phase shifts or convolutions for chirped pulse excitation to fixation states, control maps, fixation data, protocols, or the like. The computing unit 434 can control the components of the computing system 420. By way of example, the function generator 421 and the controller 422 can be controlled to automatically monitor and process the specimen 435.

The system 420 can perform ultrasound velocity measurements based on phase differences observed between transmitted pulse packet (e.g., 100-300 waves of constant wavelength) and received pulse packet after exposure to the sample tissue 435. The phase differences can be measured as an absolute phase angle difference relative to the wavelength of the base frequency of the pulse packet (e.g., 0 degrees to 360 degrees).

Figure 18:
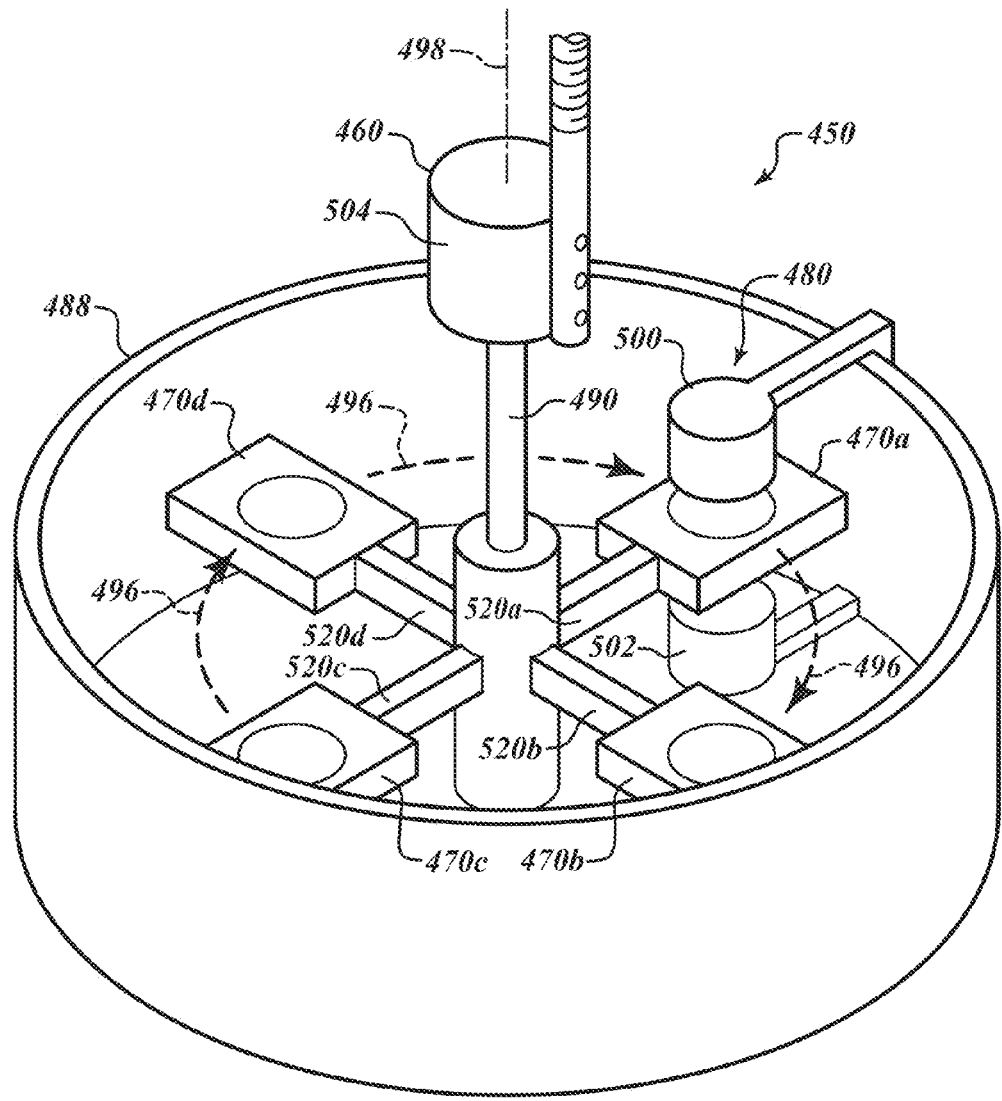
FIG. 18 is an isometric view of a processing system capable of sequentially analyzing specimens.

FIG. 18 shows a processing system 450 that includes a transport apparatus 460 configured to successively move specimen holders 470a, 470b, 470c, 470d (collectively 470) to an analyzer 480. The transport apparatus 460 includes arms 520a, 520b, 520c, 520d (collectively 520) that extend outwardly from a member 490. The specimen holders 470 are carried by the respective arms 520. The specimen holder 470a is shown in the analyzer 480. To move the specimen holder 470d into the analyzer 480, the member 490 is rotated (e.g., in a clockwise direction indicated by arrows 496) about an axis of rotation 498 until the specimen holder 470d is between a transmitter 500 and a receiver 502 of the analyzer 480. A positioning mechanism in the form of a drive motor 504 can rotate the member 490 based on feed back from the analyzer 480. A computing device, for example, can control the motor 504 in response to signals from the analyzer 480. The motor 504 can be a drive motor, stepper motor, or the like.

A fixative (not shown in FIG. 18) held in a container 488 can fix the specimens in the specimen holders 470. Advantageously, when a path between the transmitter 500 and the receiver 502 is unobstructed, the acoustic characteristics of the media can be evaluated to determine any changes in sound speed due to the media. The processing system 100 can then be recalibrated. If the distance between the transmitter 500 and the receiver 502 is about 50 millimeters, signals can be sent every few milliseconds because the total travel time may be about 40 µs. The frequency of transmitted acoustic energy, focal properties of transmitters, and geometry and dimensions of the transmitters can be selected to achieve a desired total travel time. Any number of signals can be sent at regular or irregular intervals to determine any processing changes that may affect the collected data.

The specimens can be individually monitored while all of the specimens undergo fixation. The processing system 450 can also have any number of analyzers 480. For example, the processing system 450 can have analyzers that are spaced apart from each other such that the specimen holders 470 are successively delivered to the analyzers. The analyzers may have different types of components to evaluate different properties of the specimens.

Figure 19:
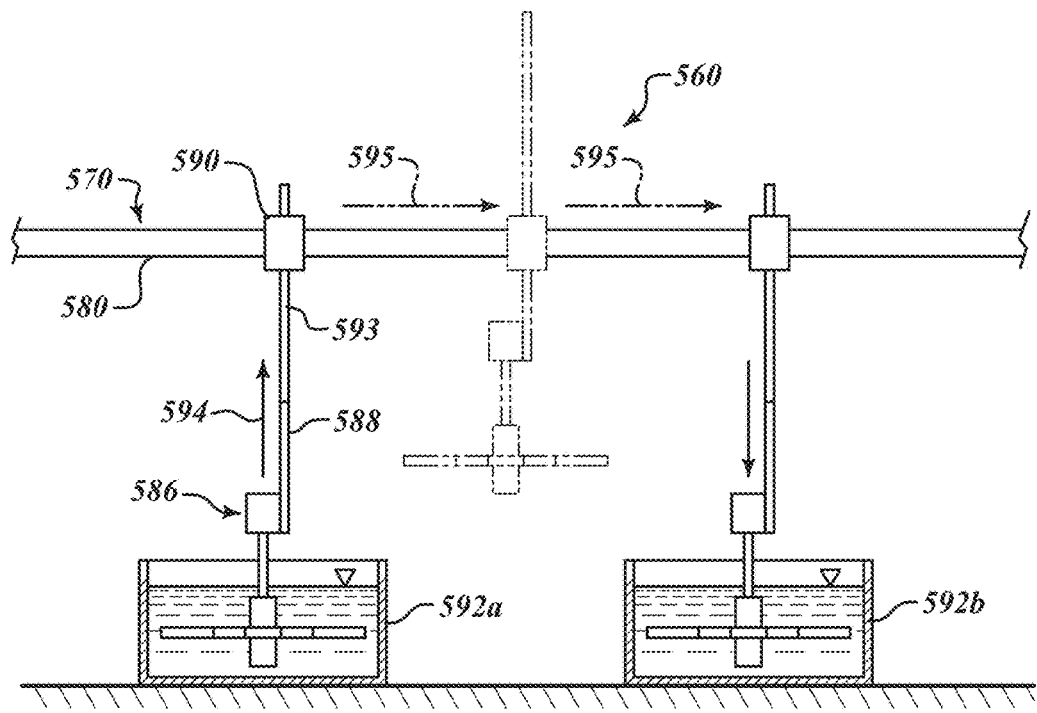
FIG. 19 is an elevated, partial cross-sectional view of a processing system capable of performing multiple treatments on specimens, in accordance with one embodiment.

FIG. 19 shows a processing system 560 for automatically processing specimens in different fluids. The samples can be processed in batches such that each batch of specimens is processed using the same protocol. The system 560 includes a drive apparatus 570 with a rail 580 and a transport apparatus 586 movable along the rail 580. The transport apparatus 586 includes a vertically movable rod 588 connected to a carriage 590. The carriage 590 can slide along the rail 580 to move the transport apparatus 586 between containers 592a, 592b.

To move the illustrated transport apparatus 586 to the container 592b, the carriage 590 raises the transport apparatus 586 from a lowered position 593, as indicated by an arrow 594. Once the transport apparatus 586 is out of the container 592a, the carriage 590 can move along the rail 580, as indicated by arrows 595. Once the raised transport apparatus 586 is above the container 592b, the carriage 590 lowers the transport apparatus 586 into the container 592b. In this manner, specimen holders carried by the transport apparatus 586 can be submerged in processing media in the containers 592a, 592b. In some embodiments, including the illustrated embodiment, the container 592a contains a fixative, and the processing media in the container 592b is a clearing agent.

Figure 20:
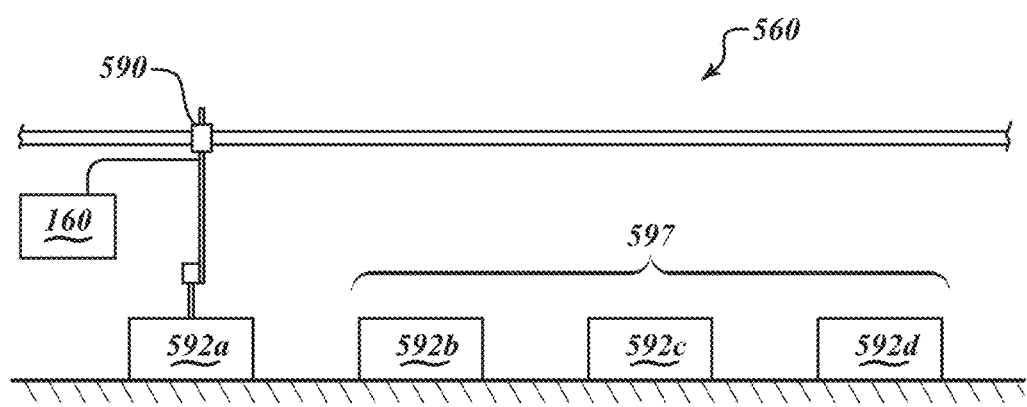
FIG. 20 is a side elevational view of a processing system capable of performing multiple treatments on specimens, in accordance with one embodiment.

Any number of containers can be used with the illustrated processing system 560. FIG. 20 shows a modified embodiment of the processing system 560 with containers 592a, 592b, 592c, 592d (collectively 592). A carriage 590 can carry the specimens sequentially into the containers 592, which can contain a wide range of different types of processing medias, including fixatives, clearing agents (e.g., xyline or the like), infiltrations, dehydration agents, reagents, or the like. The illustrated processing system 560 includes a tissue preparation unit 597 comprising the containers 592b, 592c, 592d.

The container 592a can contain a fixative in which specimens are fixed. After fixing, the specimens can be sequentially delivered to the containers 592b, 592c, 592d which each contain a tissue preparation media, such as a dehydration agent, a clearing agent, an infiltration agent, or the like. In some embodiments, the computing device 160 can generate a tissue preparation protocol used to process the specimens in the container 592b, which contains a dehydration agent, such as alcohol. The tissue sample can be treated with a clearing agent in the container 592c. The specimen can be treated with an infiltration agent in the container 592d. The tissue preparation protocol can include length of processing times in the processing media, composition of the processing media, temperature of the processing media, or the like. Of course, different specimens with different types of tissue, dimensions, etc. can be processed for different lengths of time. As such, different tissue preparation protocols can be generated for different tissue types to ensure that the specimens are adequately prepared for embedding.

Figure 21:
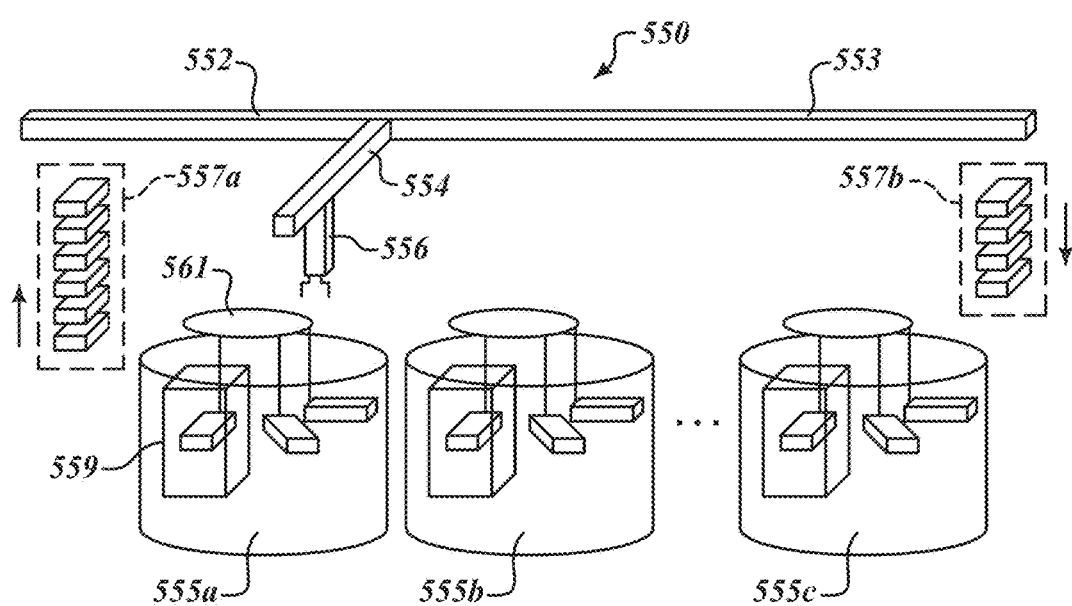
FIG. 21 is a side elevational view of a processing system capable of individually processing tissue samples.

FIG. 21 shows a processing system 550 for automatically processing specimens and random access loading. STAT processing can reduce the time to diagnosis for high priority samples. The processing system 550 includes a drive apparatus 552 with a rail 553 and a handing device, illustrated as a 3-axis handling robot 554, movable along the rail 553. The 3-axis handling robot 554 includes a lifter 556 for transporting specimen holders to stations, illustrated as containers 555a, 555b, 555c (collectively 555). Specimen holders can be loaded at any time from a feed mechanism 557a (illustrated in dashed line) to the container 555a. Each container 555 includes a rotary positioning mechanism 561 for sequentially positioning specimens in a channel of an analyzer 559. The specimens can be monitored to ensure proper fixation. New samples can be automatically loaded at any time. In contrast to the batch operations discussed in connection with FIGS. 18-20, once a specimen is processed, it can be removed from the container while other specimens are processed.

Specimen holders can be placed in the first processing container 555a holding cold formalin or warm formalin. The specimens can be sequentially fed through a measurement channel (e.g., an ultrasound TOF measurement channel) in order to track the progression of the reaction in the container 555a. Once a tissue sample process is complete, the handling robot 554 can remove the specimen holder with the processed sample and move it to the next processing container or station 555b. The individual handling of specimen holders can allow faster fixing of samples to be moved earlier and bypassing of slower fixing samples, thereby providing custom processing times optimized per individual sample. This increases the total throughput of the system 550.

By way of example, one specimen holder carrying a fatty tissue can be processed using a fatty tissue preparation protocol and another specimen holder carrying muscle tissue can be processed using a muscle tissue preparation protocol. The different protocols can provide different processing times, different waves (e.g., different frequencies, different waveforms, etc.), different compensation algorithms, or the like. A protocol can be selected based on individual sample treatment requirements due to size variations, type of tissue sample, history of tissue samples, and/or other characteristics of samples. If the size/material of sample changes, another protocol can be selected by the operator and/or automatically selected by a computing system.

Information collected from samples can be used for processing subsequent samples. Processing time information obtained from a sample can be used to determine a priori the processing times for the next station or monitoring (e.g., ultrasound TOF monitoring). The specimen holder can include information (e.g., machine-readable code) readably by readers at the containers 555a-c. Once processing is complete, the samples may be infused with paraffin and can be unloaded into an output queue 557b. The processed specimens can be picked up at convenient times.

Figure 22:
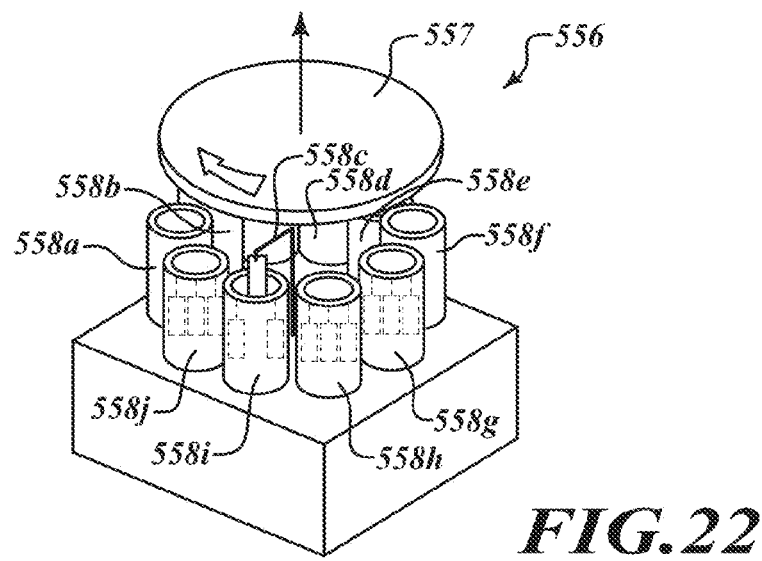
FIG. 22 is an isometric view of an analyzer with a rotary drive system.

FIG. 22 shows a processing system 556 that provides random access to tissue samples. The processing system 556 includes a carousel positioning mechanism 557. A lifter 558 can grip and carry specimen holders or specimens between processing stations 558a-j, illustrated as open containers.

Figure 23:
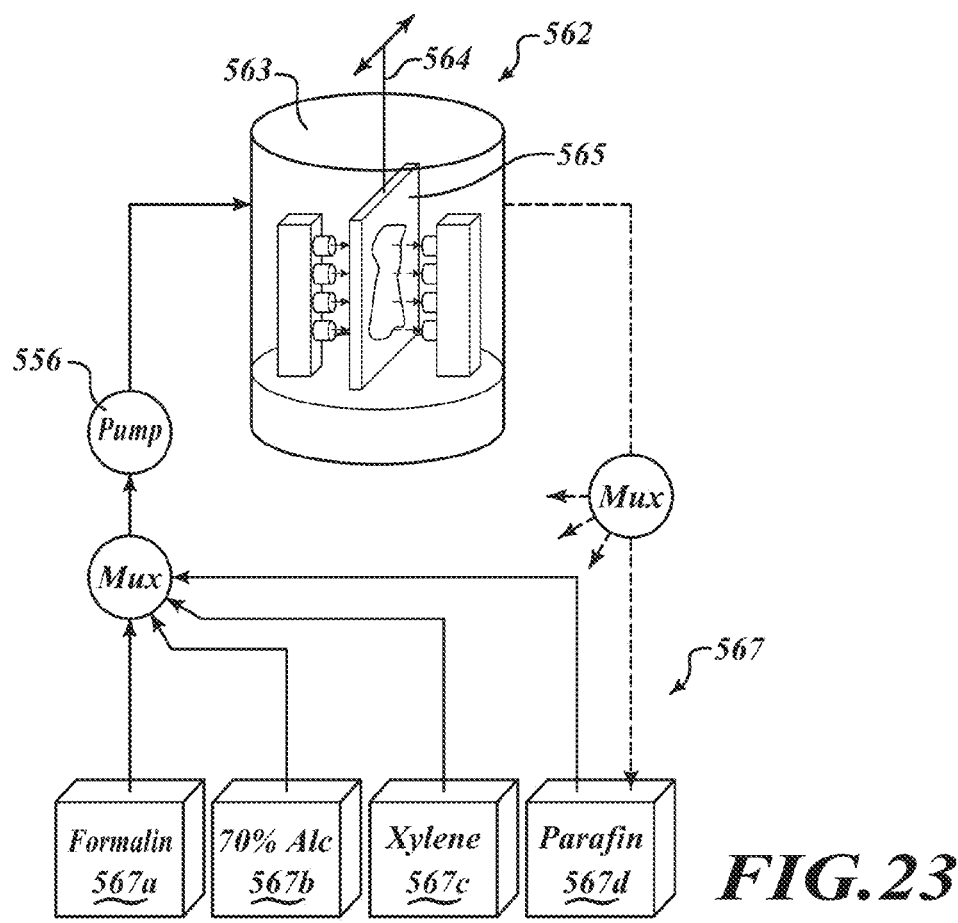
FIG. 23 is a processing system capable of fixing and embedding a tissue sample.

FIG. 23 shows a station 562 with a single closed reaction chamber 563 and a positioning system in the form of a mechanical drive mechanism 564. A pump 566 can exchange media. A valve/multiplexer system 567 fluidically couples containers 567a-d. Additionally or alternatively, one or more vacuum devices can be used to transport fluids between containers. Any number of multiplexer pumps, valve systems, vacuum devices, conduits, thermal devices, containers, or other fluid devices can be used to manage processing media.

Figure 24:
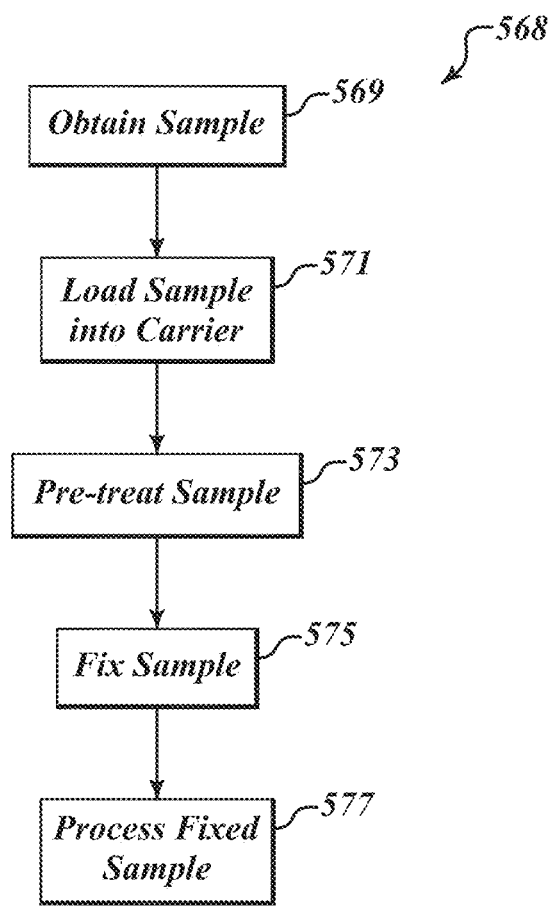
FIG. 24 is a flow diagram of an exemplary method of processing a specimen.

FIG. 24 is a flow chart of a workflow system 568. Generally, the workflow system 568 is used to track samples with the corresponding subject identification from surgery through tissue processing. Information obtained from the samples can be included in the subject's records and can facilitate generation of reports (e.g., reports used for diagnosis, patient monitoring, billing, etc.), an audit trail (e.g., an audit trail of specimen handling steps), a processing parameter log (e.g., a log that could be printed and as a quality record at the end of the processing), or the like.

Samples can be monitored by an active (or passive) RFID tag embedded in or otherwise coupled to the specimen holder. Once the sample is acquired, it can be transferred to the specific specimen holder. In some protocols, the specimen can be stored in a cooled container (−4° C.) with 10% neutral buffered formalin by volume. Upon entry into the specimen holder and container, the RFID tag can be programmed, such as by swiping past a communication device (e.g., reader/writer device) to track the time and allow association of the patient ID to the unique RFID device ID. Alternatively, a bar coding scheme with a linked database or other machine-readable code could be used, if needed or desired.

At 569, a sample is taken from a subject. The sample can be a tissue sample removed from a subject using a needle, biopsy tool, or the like and can be a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can also be used to obtain the sample.

At 571, the sample is loaded into a specimen holder with machine-readable code. The machine-readable code can be any type of optical symbology, magnetic pattern or electromagnetic or electrostatic signal having information content. For example, information content may relate to sample identity, sample origin, sample chain of custody, instructions for processing a sample, information regarding the characteristics of a sample, test results for a sample, images of the sample and the like.

The workflow system 568 can include any number of communication devices capable of reading and/or writing information. A communication device can be any type of machine that can decipher, translate or interpret the information contained in a machine-readable code, for example, a device that converts the code into commands for performing an automated procedure or presenting the information in a human-readable or human-interpretable form. A communication device can be a reader compatible with one or more different types of machine-readable code, such as optical symbologies, bar codes, and the like. Examples of optical symbologies include characters, bar codes and dataglyphs. Particular examples of bar codes include linear bar codes, multi-dimensional bar codes such as 2D stacked symbologies and 2D matrix symbologies, and composite bar codes such as reduced-space symbologies. Even more particular examples of 2D optical symbologies include PDF417, data matrix, maxicode, vericode, codablock, aztec code, code 16K and QR code. Bar code readers for these and any number of other optical symbologies are well known. Where the machine-readable code comprises characters (e.g., alphanumeric characters such as English text and Arabic numbers) the code reader can be an optical character reader (OCR). Magnetic stripes are only one example of a device that can store information in the form of a magnetic pattern. An example of an electromagnetic code is an RFID tag. RFID tags typically include a small metallic antenna and a silicon chip, and can be active or passive. RFID code readers are well known, and typically include an antenna and a transceiver that receives information from the RFID tag. The information content of an RFID tag can be fixed or changeable. In another embodiment, the communication device is a code reader that includes a CCD camera and the CCD camera can be used for simultaneous detection of samples and reading of a bar code or characters. Other examples of machine-readable codes that can be used include Bragg-diffraction gratings and micro- or nano-bar codes (such as spatial and spectral patterns of fluorescent particles or spatial patterns of magnetic particles).

At 573, the sample can be pretreated to facilitate subsequent processing. The sample can be pre-treated with formalin or other media. Cold formalin can pre-treat the sample without causing appreciable cross-linking. The pre-treatment process can include a delivery process in which the formalin travels through the sample and are discussed in connection with FIGS. 39-42.

At 575, the sample can be delivered to a processing system and undergoes a fixation process. The sample can be monitored during fixation. Processing times, fixation history, tissue characteristics, or other histology information can be used to adjust processing to ensure proper histology tissue processing.

At 577, the tissue can be prepared for examination or storage. The sample can be embedded, sectioned, and transferred onto a microscope slide for subsequent processing and analyses, such as staining, immunohistochemistry, or in situ hybridization. To section a tissue sample for optical microscope examination, a relatively thin strip of tissue can be cut from a large tissue sample so that light may be transmitted through the thin strip of tissue. A microtome can cut the specimen into thin sections, for example, slices on the order of about 5 microns to about 6 microns thick. Each section can include a portion of the tissue sample and some of the embedding material. The microtome and any other equipment (e.g., a staining station, an embedding station, an oven, etc.) used in the processing system 556 can include communication devices to read and/or write information to the specimen holder.

The tissue sample can be transferred onto a microscope slide, which can include machine-readable code. In some embodiments, the cut sections are floated on water to spread or flatten the sections. If the sections are pieces of paraffin embedded tissue, the sections can be floated on a warm bath to keep the sections in generally flat configurations, thereby reducing or preventing folding, creasing, or bending. A microscope slide is inserted into the warm bath. A front surface of the slide is used to pick up the tissue samples. To examine multiple tissue samples (e.g., a set of tissue samples, each taken at a different location in a subject) using a single slide, a plurality of the tissue samples may be sequentially floated onto the slide. These wet slides are then dried using the slide dryer and coverslipped.

FIG. 25 shows an analyzer 598 that includes a transmitter unit 599 with an array of transmitters 600a, 600b, 600c, 600d (collectively 600) and a receiver unit 601 with an array of receivers 602a, 602b, 602c, 602d (collectively 602). Transmitters 600 are aligned with respective receivers 602. The pairs of transmitters 600 and receivers 602 can monitor different sections of a specimen 604. The number of transmitters/receivers, positions of the transmitters/receivers, and the spatial resolution of the analyzer 598 can be selected based on the size of the specimen 604. In order to expand the spatial resolution for relatively small biopsy cores, the focal diameters of the transmitters 600 can be relatively small. In certain embodiments, the focal diameters can be in a range of about 2 millimeters to about 5 millimeters. Other ranges of focal diameters are also possible. Other means of adjusting the focal properties may include, without limitation, acoustic lenses or apertures in front of the transmitters/receivers. The focal diameters of the transmitters 600 can overlap to ensure that the entire specimen 604 is analyzed. In other embodiments, the focal diameters of the transmitters 600 can be spaced apart from one another.

To analyze the specimen 604, a specimen holder 606 can be moved through a gap 608 between the transmitter unit 599 and the receiver unit 601. In some embodiments, the specimen holder 606 is moved through the gap 608 using a transport apparatus. In other embodiments, the specimen holder 606 is manually inserted into the gap 608.

FIG. 26 shows an analyzer 620 with a transmitter unit 621 and a receiver unit 623. The transmitter unit 621 includes transmitters 622a, 622b, 622c, 622d (collectively 622). The receiver unit 623 includes receivers 624a, 624b, 624c, 624d (collectively 624). The illustrated linear array of transmitters 622 and linear array of receivers 624 can scan a specimen 630.

Different combinations of transmitters and receivers can be used to provide different sound paths through tissue samples. As shown, a transmitter 640 can communicate with a receiver 642 such that the sound paths between the transmitters 622 and receivers 624 is generally perpendicular to a sound path between the transmitter 640 and the receiver 642. Thus, measurements can be taken in different directions. Such embodiments are well suited for analyzing specimens with anisotropic properties. The number, types, orientations, and positions of transmitters/receivers can be selected based on the characteristics of the specimen.

Figure 27:
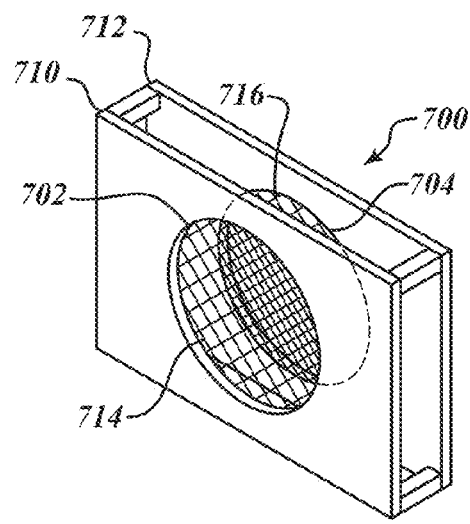
FIG. 27 is an isometric view of a specimen holder, in accordance with one embodiment.

FIG. 27 shows a specimen holder 700 that includes plates 710, 712 that are spaced apart and generally parallel to one another. Apertures 702, 704 facilitate delivery of acoustic waves to a tissue sample. A specimen can be sandwiched between the plates 710, 712 and held in a substantially flat configuration. Acoustic energy can travel generally perpendicular to the plates 710, 712 and can pass through the aligned apertures 702, 704.

Barrier elements 714, 716 can block the apertures 702, 704, respectively. Each of the barrier elements 714, 716 can include, without limitation, a mesh, a perforated material, a web, a grate, a screen, foil, fabric, or any other structure or material through which acoustic waves can travel with minimal, limited, or substantially no attenuation. The barrier elements 714, 716 can thus keep the specimen within the specimen holder 700. The barrier elements 714, 716 can also be permeable to ensure that a sufficient amount of the specimen is contacted by the processing media. In some embodiments commercially available biopsy tissue cassettes may be utilized.

Figure 28:
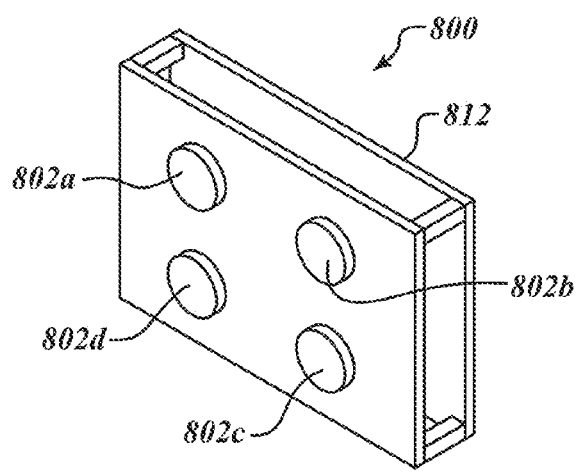
FIG. 28 is an isometric view of a specimen holder with transmitters and receivers.
Figure 29:
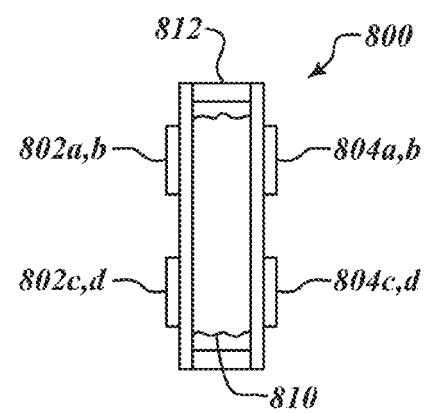
FIG. 29 is a side elevational view of the specimen holder of FIG. 28.

FIGS. 28 and 29 show a specimen holder 800 that is generally similar to the specimen holder 700, except as detailed below. FIG. 29 shows the specimen holder 800 holding a specimen 810. The specimen holder 800 includes transmitters 802a, 802b, 802c, 802d (collectively 802) and receivers 804a, 804b, 804c, 804d (collectively 804). The transmitters 802 and receivers 804 can contact or be proximate to the specimen 810 to minimize signal attenuation and other problems often associated with transmitting across relatively large distances, and to minimize or limit attenuation attributable to processing media (e.g., if a gap is formed between the specimen 810 and the walls of the holder 800).

The transmitters 802 and receivers 804 can be coupled to a main body 812. In certain embodiments, the transmitters 802 and receivers 804 are permanently coupled to or integrated into the main body 812. In other embodiments, the transmitters 802 and receivers 804 are removably coupled to the main body 812 to allow components to be interchanged or removed for inspection, maintenance, or the like. To facilitate physical contact between the specimen 810 and processing media, the specimen holder 800 can have any number of apertures and can be made of a permeable or semi-permeable material.

The tissue sample holder 700 of FIG. 27 and the specimen tissue holder 800 of FIGS. 28 and 29 can be used with the processing system 100 of FIGS. 1 and 2, the processing system 450 of FIG. 18, the processing systems 560 of FIGS. 18-20, the processing system 550 of FIG. 21, etc. Processing systems can thus be configured to receive a wide range of different types of specimen holders with or without transmitters or receivers, sensors, apertures, or the like.

Figure 30:
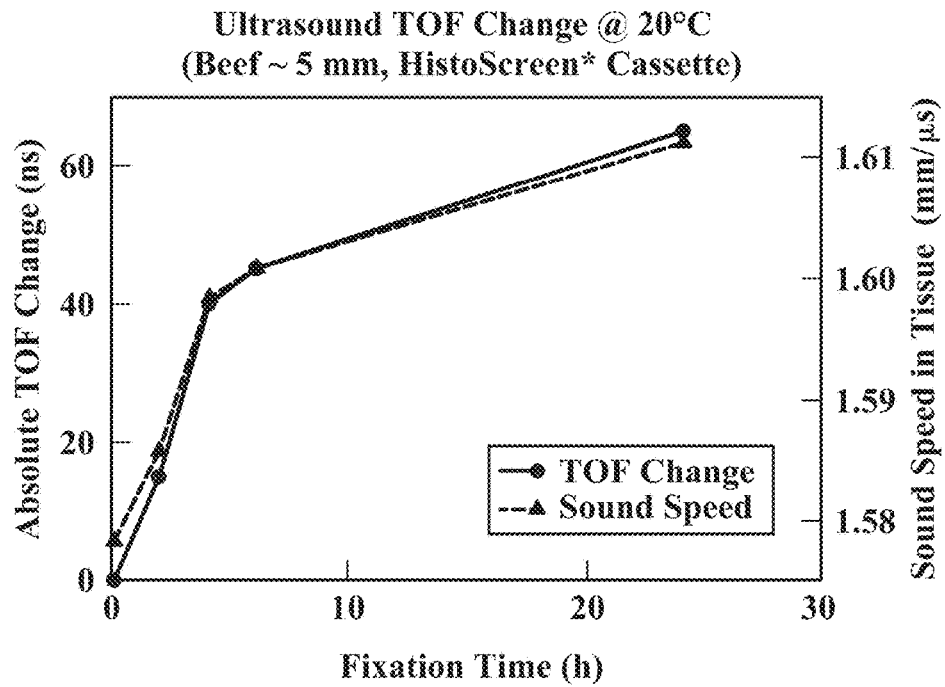
FIG. 30 is a plot of fixation time versus sound of speed in tissue and absolute TOF change for beef tissue.
Figure 31:
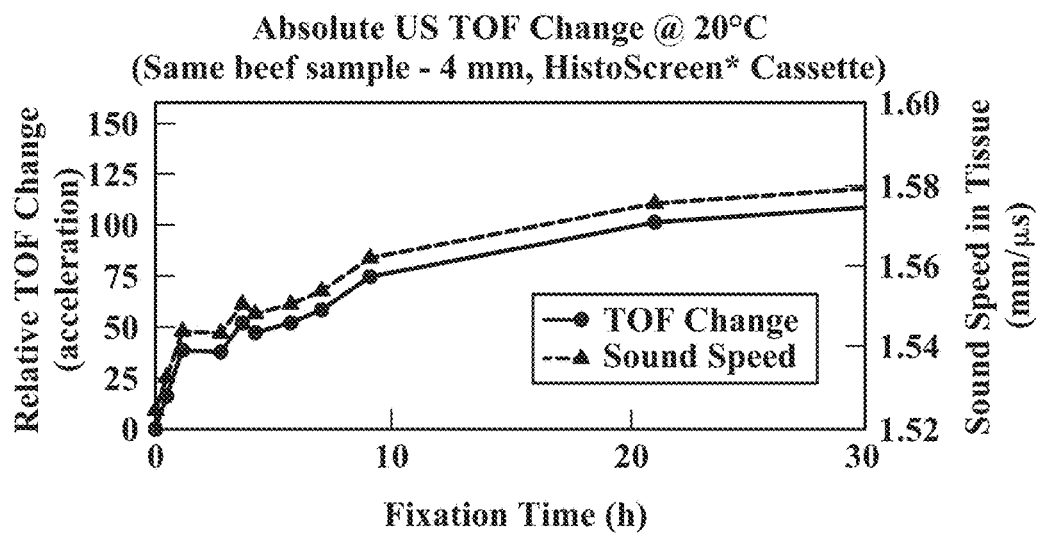
FIG. 31 is a plot of fixation time versus sound speed and relative TOF change for beef tissue.
Figure 34:
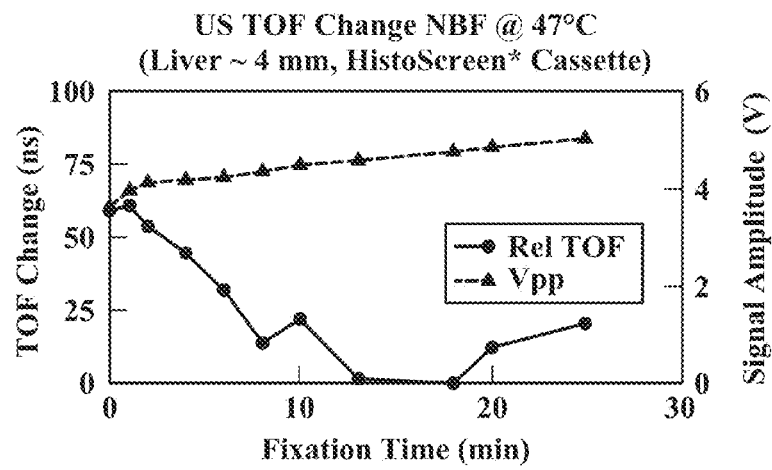
FIG. 34 is a plot of fixation time versus signal amplitude and TOF change for liver tissue.
Figure 35:
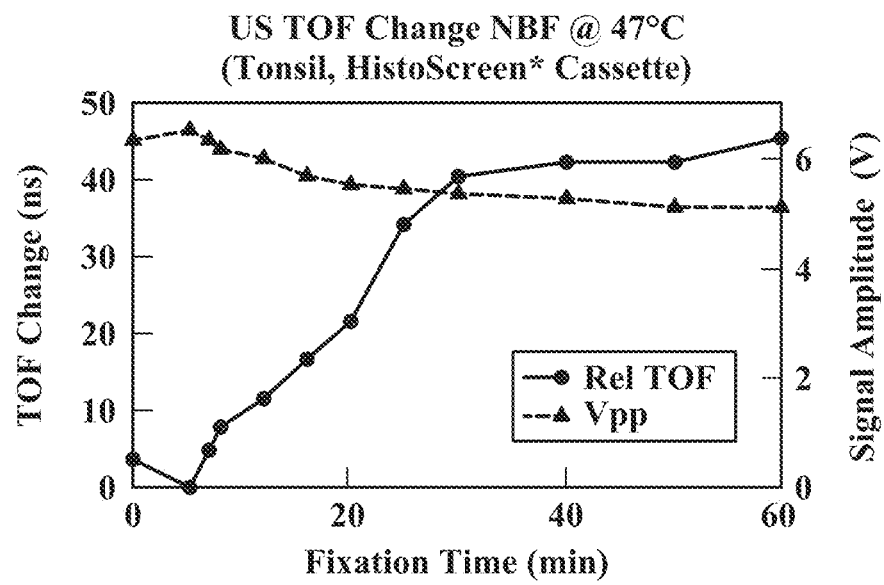
FIG. 35 is a plot of fixation time versus signal amplitude and TOF change of human tonsil tissue.
Figure 36:
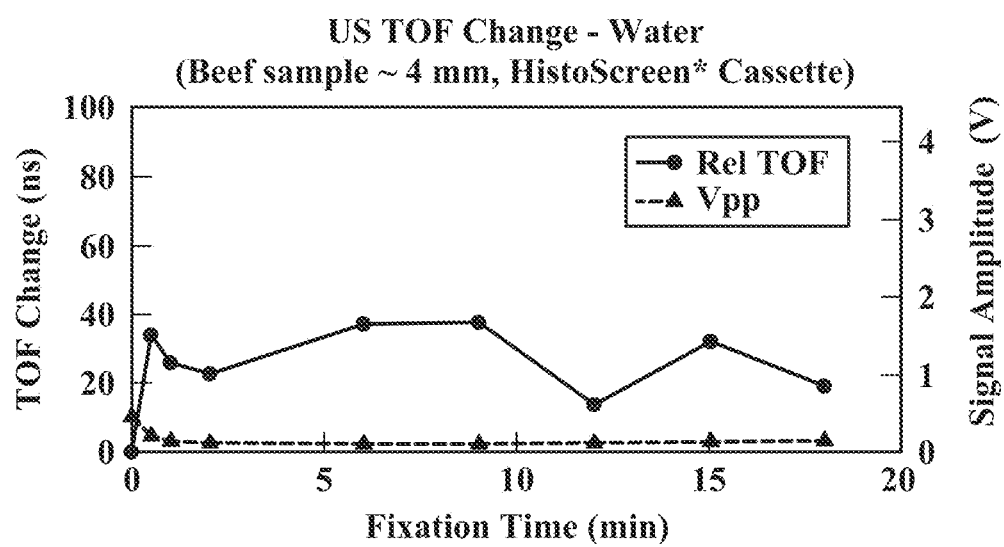
FIG. 36 is a plot of fixation time versus signal amplitude and TOF changes for beef tissue.

FIGS. 30-36 show measurements generated from a processing system analyzing specimens. FIGS. 30 and 31 show measurements taken with NBF at room temperature (e.g., about 20° C.). A heated bath of NBF was used to obtain the measurements of FIGS. 32-35. Heated baths can be used to reduce fixation times. FIG. 36 shows a negative control run in water.

Referring to FIG. 30, beef muscle was cut into approximately 4 mm to 5 mm thick pieces and fixed in time increments of about less than 1 hour, 2 hours, 4 hours, 6 hours, and 24 hours. TOF was measured while the fixative was kept at room temperature. As shown, equivalent sound speed change was observed from about 1,580 m/s to about 1,610 m/s.

FIG. 31 shows fixation time versus sound speed and relative TOF change. The measurements were obtained using a sample of beef muscle with a thickness of about 4 mm. Inline monitoring was used to monitor fixation in a bath of NBF for about 21 hours. Equivalent sound speed change was observed from about 1,520 m/s to about 1,580 m/s.

Figure 32:
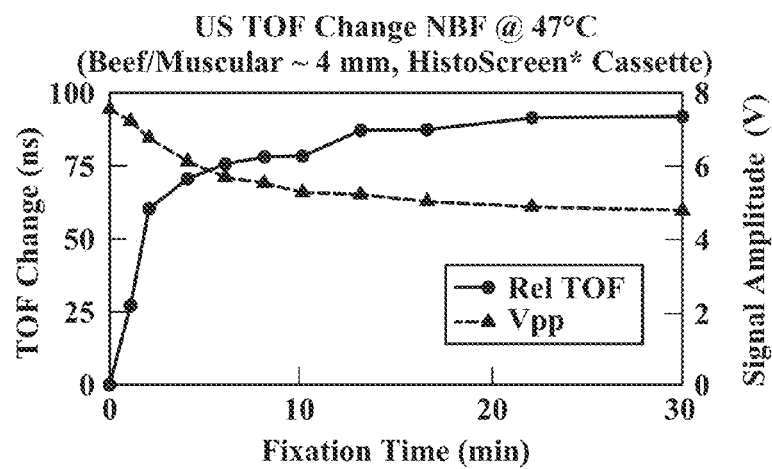
FIG. 32 is a plot of fixation time versus signal amplitude and TOF change for beef tissue.

FIG. 32 shows fixation time versus signal amplitude and TOF change in a heated bath of NBF. A tissue sample of beef muscle tissue was cut across its fibers. The tissue sample had a thickness of about 4 mm and was fixed in a heated bath of NBF. The NBF bath was kept at a temperature of about 47° C. with about +/−1° C. control.

Figure 33:
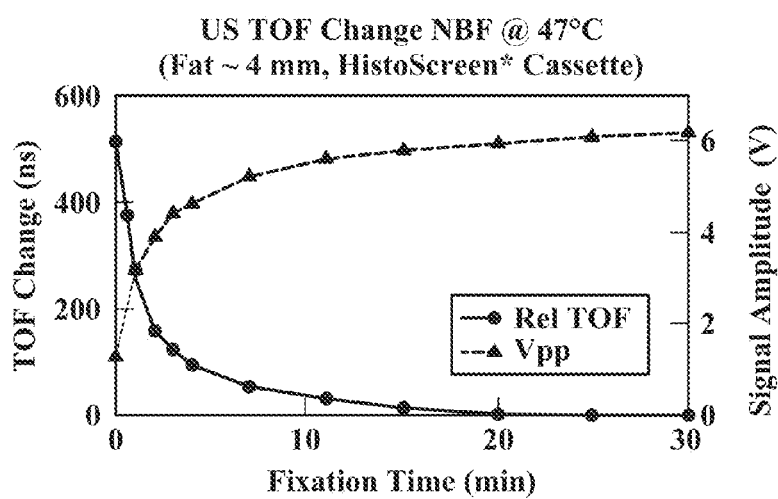
FIG. 33 is a plot of fixation time versus TOF change and signal amplitude for fat tissue.

FIG. 33 shows fixation time versus signal amplitude and TOF change of fat tissue in a heated bath of NBF. The fat tissue had a thickness of about 4 mm. The heated NBF bath was maintained at a temperature of about 47° C. with about +/−1° C. temperature control.

FIG. 34 shows fixation time versus signal amplitude and TOF change of liver tissue in a heated bath of NBF. A sample of liver tissue with a thickness of about 4 mm was fixed in the heated NBF bath maintained at about 47° C. with about +/−1° C. temperature control.

FIG. 35 shows fixation time versus signal amplitude and TOF change of human tonsil tissue in a heated bath of NBF. The tissue sample was fixed using a heated NBF bath maintained at about 47° C. with about +/−1° C. temperature control.

FIG. 36 shows fixation time versus signal amplitude and TOF change of muscular beef tissue in a negative control bath of deionized water. The tissue sample had a thickness of about 4 mm. The bath was heated and maintained at about 47° C. with about +/−1° C. temperature control.

Two protocols were used to analyze different types of tissue. In one protocol, different samples were fixed for different lengths of times and kept at about room temperature. Signal amplitude was measured in close succession. In the other protocol, the same samples were continuously monitored and kept at elevated temperatures until signal levels reached a plateau.

Both protocols produced similar results, with the elevated temperature processing providing faster fixation. The measurements (e.g., sound speed measurements) at higher temperatures are subject to more fluctuations due to temperature gradients in the media between the transmitter and the receiver and warm-up effects from the sample tissue and the specimen holder, which were initially introduced at room temperature and had to equilibrate. In another protocol, a specimen and specimen holder were briefly (e.g., about 5 minutes to about 10 minutes) warmed up externally to about 47° C. before being inserted into the measurement channel with similar results.

Figure 37:
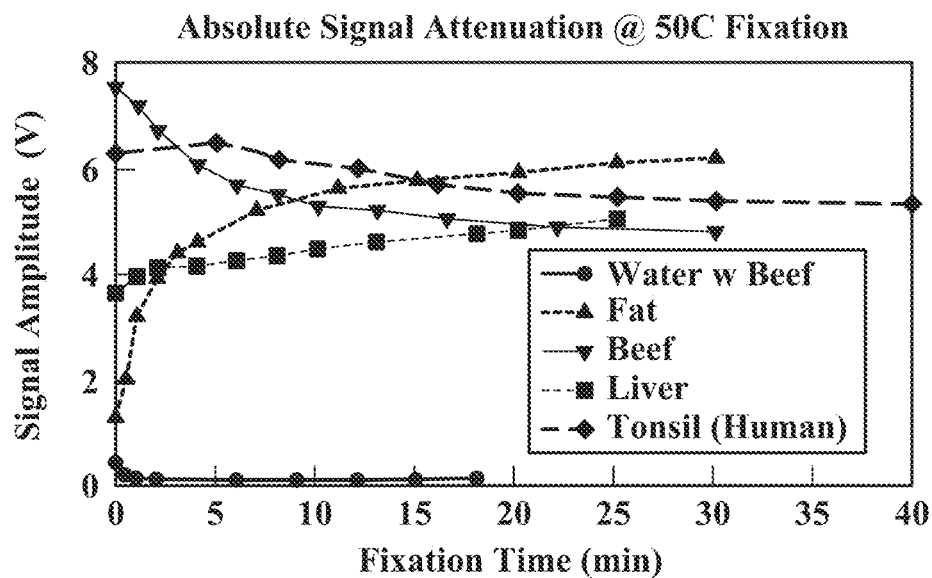
FIG. 37 is a plot of fixation time versus signal amplitude for different types of tissue.
Figure 38:
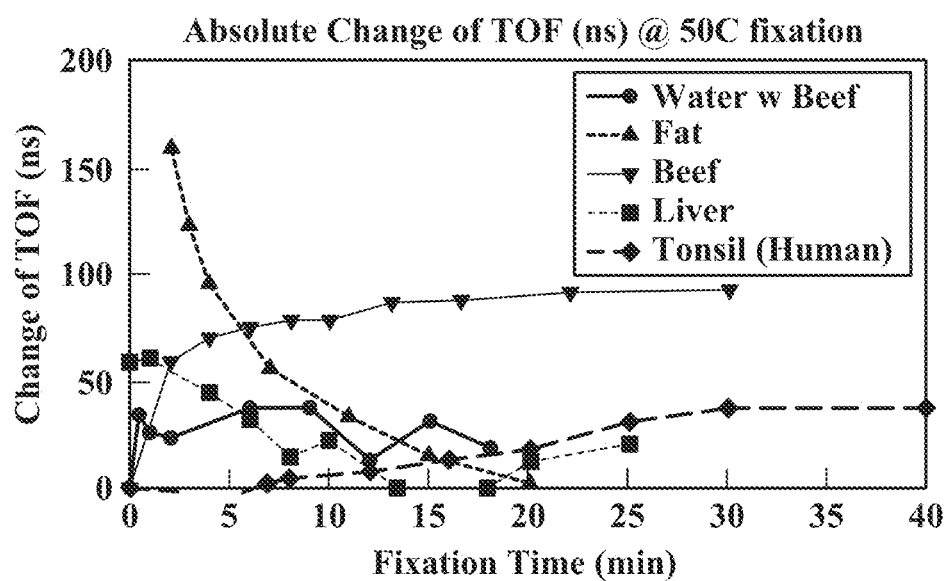
FIG. 38 is a plot of fixation time versus change of TOF for different types of tissues.

Results of TOF measurements and signal attenuation are shown in FIGS. 37 and 38 for comparison between different types of tissue. FIG. 37 shows fixation time versus signal amplitude for beef in water (which serves as a negative control) and fat, beef, liver, and tonsil in a fixative. The fixative was maintained at a temperature of about 50° C. There is an increase of the received amplitude in fatty tissue. This may be due to better transmission capabilities, changes in density, combinations thereof, or the like due to the perfusion of the fixative and resulting cross-linking.

FIG. 38 shows fixation time versus change of TOF for different types of tissue maintained at about 50° C. The fatty tissue responded with exponential decay of the sound speed change during perfusion and/or fixation. This may be because of a negative temperature coefficient of fat and the warming effects of the tissue due to elevated temperature testing. The muscular tissue responded with an exponential growth change of the sound speed mostly due to cross-linking. The growth change may also be increased due to elevated temperatures. FIGS. 30 and 31 show a similar increase of about 60 ns to about 100 ns (or about 60 m/s in sound speed) observed at room temperature, and may be related to fixation.

Table 3 below shows sound speeds in different types of specimens. The specimens had a thickness of 4 mm and were fixed with a fixative maintained at about 47° C.

TABLE 3

| Tissue type | Unfixed Speed at 47° C. [m/s] | Fixed Speed at 47° C. [m/s] | Sound speed change [m/s] | Signal Amplitude Change [%] |
| --- | --- | --- | --- | --- |
| Fat (beef) | 1,687 | 1,387 | −308 | +381% |
| Muscle (beef) | 1,618 | 1,681 | +63 | −58% |
| Liver (calf) | 1,767 | 1,737 | −30 | −38% |
| Tonsil (human) | 1,672 | 1,702 | +30 | +27% |

If the tissue type of a specimen is known, the sound speed changes (e.g., increases in sound speed, decreases in sound speed, or combinations thereof) can be used to determine the tissue type. For example, if a specimen of an unknown tissue type has an unfixed speed of about 1,687 m/s and the sound speed which decreases as the tissue is fixed, it can be concluded that the tissue may be fat tissue from beef. Of course, the unfixed sound speed of the tissue can be compared to the fixed sound speed to determine the tissue type with a high degree of accuracy. Different types of tissue samples have different characteristic sound speeds.

Figure 39:
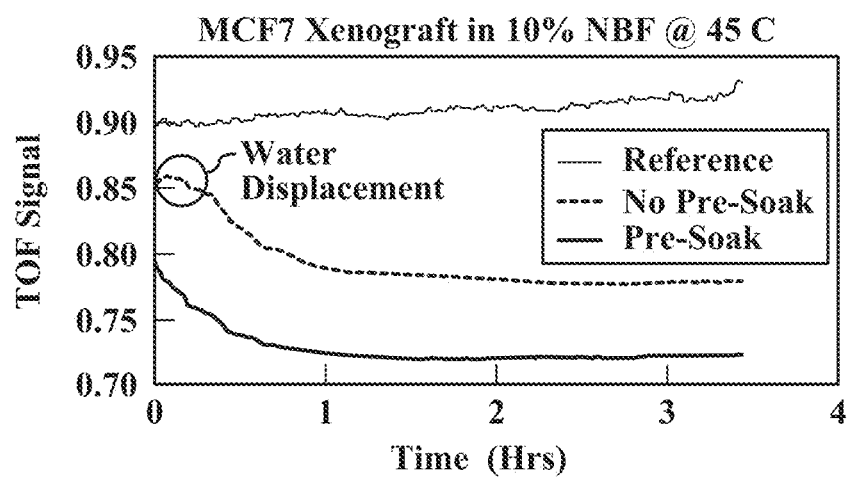
FIG. 39 is a plot of time versus a time of flight signal for a presoaked sample and a fresh sample.

Samples can be pre-treated to facilitate fixation (e.g., enhance fixation consistency, reduce fixation time, etc.) and/or monitoring. In some protocols, a sample can be soaked in media to manage the effects of perfusion through the sample. If the sample is fixed using formalin, the sample can be pre-soaked in formalin to ensure sufficient diffusion of formalin into the inner sample regions without substantial amounts of cross-linking. FIG. 39 shows time versus a TOF signal for different tissue samples. The pre-soaked tissue sample was submersed in cold formalin at 4° C. for about 2 hours. The pre-soaked sample was then submerged in high temperature formalin bath (e.g., a bath of 10% NBF at about 45° C.) to cause cross-linking and accelerate the fixation process. The pre-soaked curve shows that the TOF signal gradually decreases as the sample is fixed. If the sample is processed with glycerol solution, the sample can be pre-soaked in glycerol solution or other type of media with characteristics similar to the characteristics of glycerol solution.

Pre-soaking can minimize, limit, or substantially eliminate the effects of water displacement that significantly changes the acoustic characteristics of the tissue sample. A comparison of the pre-soaked curve (or media delivery curve) and the not pre-soaked curve shows that pre-soaking limits or substantially eliminates changes in TOF attributable to media perfusion causing displacement of lower density water in the tissue. The initial increase in phase comparison data for the not pre-soaked tissue may be caused by media perfusion (e.g., formalin diffusion) into the tissue, thereby displacing lower density water with higher density formalin (e.g., due to contained phosphates). The displacement phase is typically followed by the cross-linking phase, as indicated by rapidly declining or increasing TOF signal. A wide range of different types of fluid perfusion processes can be monitored because most processing media causes a density change in the sample.

Temperature changes in the tissue samples can affect TOF measurements. The samples can be at a temperature that is generally equal to the temperature of the media to minimize, limit, or substantially eliminate changes in TOF attributable to density changes caused by temperature changes. If the sample is at a different temperature than the temperature of the media, thermal equilibration can be accounted for because thermal equilibrium can be achieve within a few minutes after submersion in the warm solution. For example, if a sample at 4° C. is submerged in a warm formalin bath (e.g., a bath at 45° C.), the sample can reach thermal equilibrium in less than about five minutes. Based on the tissue size and characteristics (e.g., thermal characteristics), the time to reach thermal equilibrium can be estimated.

Figure 40:
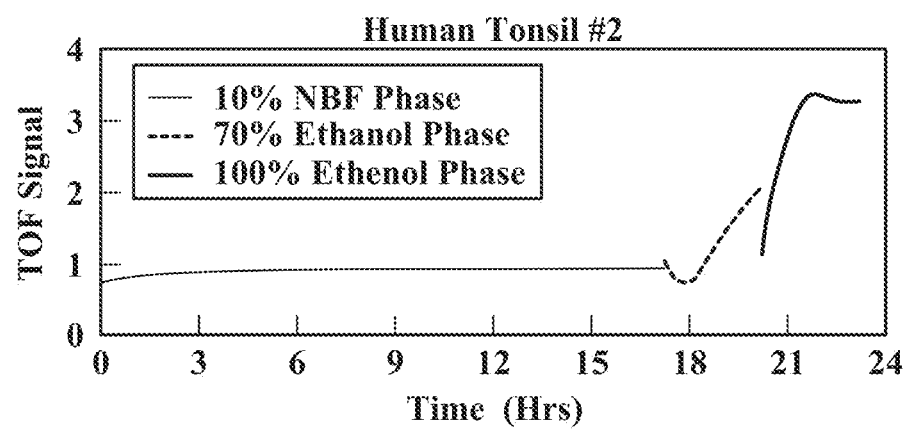
FIG. 40 is a plot of time versus a time of flight signal for a fixation and dehydration process.

Processes that cause changes to tissue structure can be monitored using the TOF measurements. For example, a dehydration process can cause measurable mechanical changes in the tissue. FIG. 40 shows time versus TOF signal for a human tonsil. The dehydration processing causes significant changes in TOF greater than the changes of TOF caused by fixation. Human tonsil was dehydrated using a 70% ethanol solution by volume and further dehydrated using a 100% ethanol solution by volume. The TOF signals shown in FIG. 40 were generated using phase detection algorithms covering multiple wavelengths.

In other dehydration protocols, tissue is exposed to gradated alcohol concentrations, to first remove phosphate buffers with a 70% ethanol/water mixture, followed by additional steps in 95% and 100% ethanol by volume to further dehydrate the fixed tissue. The tissue can undergo substantial shrinkage (e.g., more than 10% of its original volume). The amount of shrinkage can be determined using TOF measurements. The tissue shrinkage can be detected by TOF monitoring due to the resulting change in the tissue sample (e.g., tissue hardening, tissue shrinkage, etc.).

Figure 41:
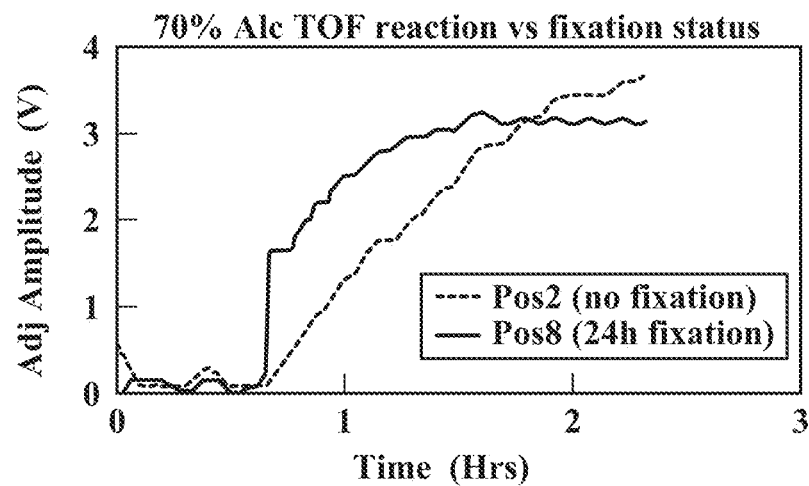
FIG. 41 is a plot of time versus amplitude of a time of flight signal for insufficiently fixed tissue and fixed tissue.

Monitoring can be used to evaluate whether samples are properly processed. FIG. 41 shows time versus TOF signals of an alcohol dehydration process. The alcohol dehydration can rely on sufficient cross-linking established during the fixation process. The resulting tissue compression during the dehydration processes can be empirically known to produce more disruptive tissue effects (such as tearing and cell and nucleus contraction) when the fixation step is omitted or too short. FIG. 41 shows differences in the TOF signal in 70% alcohol by volume of insufficiently fixed tissue versus properly fixed tissue. The overall process time of unfixed tissue in alcohol is significantly longer and the observed TOF changes are much larger than in fixed tissue (after 24 hours of standard fixation).

Figure 42:
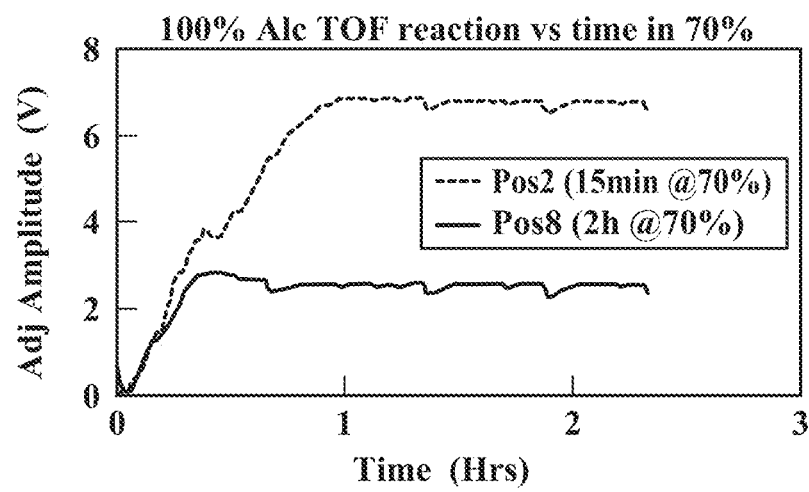
FIG. 42 is a plot of time versus time of flight signal amplitude for a tissue sample submerged for different lengths of time in formalin.

Samples can be processed successively in different media to enhance TOF measurements. A first dehydration process can be performed in a preconditioning media. For example, a sample can be submerged in a bath of 70% alcohol by volume for about 15 minutes. The partially dehydrated sample is then subjected to a second dehydration process involving submerging the partial dehydrated sample in a bath of 100% alcohol by volume. As shown in FIG. 42, preconditioning produces a much larger TOF response in the 100% alcohol bath as compared to a sample processed in a bath of 70% alcohol for about 2 hours. The response in tissue compression is likely much higher when skipping or performing for too little time the 70% alcohol step.

Compensation protocols can be used to minimize, limit, or substantially eliminate unwanted noise cause by the environmental factors. The environmental factors may include, without limitation, temperature changes due to the ambient temperature, evaporative losses, media density changes (e.g., due to chemical reactions), or the like. If the temperature of the media fluctuates, the density of the media can also fluctuate and lead to noise in the TOF measurements. A thermal device (e.g., heating/cooling device) can keep the media within a desired temperature range or at a desired temperature. Additionally, a container holding the media can be thermally insulated to minimize or limit temperature changes.

The containers can be closed to avoid evaporative losses to minimize, limit, or substantially avoid drift. Evaporation of the media can result in a gradual change in TOF over time. For example, a total change in TOF of about 25 nanoseconds can result from about 15 hours of evaporation. Lids or covers can be placed on the containers to avoid or limit evaporation. Alternatively or additionally, media can be pumped into a container to maintain a desired characteristic of the media.

Compensation schemes can be used to minimize, limit, or substantially eliminate environmental influences by using a reference channel (i.e., a position where data is taken, but the tissue or cassette is not in the way of the beam). Data values at this position can be subtracted from values at target positions.

A wide range of signal processing routines can be used to analyze the signals discussed herein. Filtering routines, compression routines (e.g., true pulse compression routines), cross-correlation routines, auto correlation signal recovery (especially in noisy environments), or the like can be utilized. Signal processing is especially well suited when samples are in relatively small containers in which there may be standing waves, reflections, and echoing. Signal processing routines can thus be selected to significantly improve signal-to-noise ratios.

FIG. 39 shows the time of flight signal in a reference sample, a pre-soak sample, and a sample that has not been subjected to a pre-soak process. As shown with the no pre-soak curve, the TOF signal generally increases immediately after submerging a tissue sample into a non-buffered formula and bath at a temperature of about 45° C. After about six to ten minutes, the TOF signal gradually decreases similar to the pre-soaked specimen. As indicated in FIG. 9, the TOF signals between the pre-soaked and non-pre-soaked samples can generally correspond to water being displaced by the formalin. Because the formalin and the water have different sound transmissibilities, the TOF signals change as the formalin replaces the interstitial in the sample.

Figure 43:
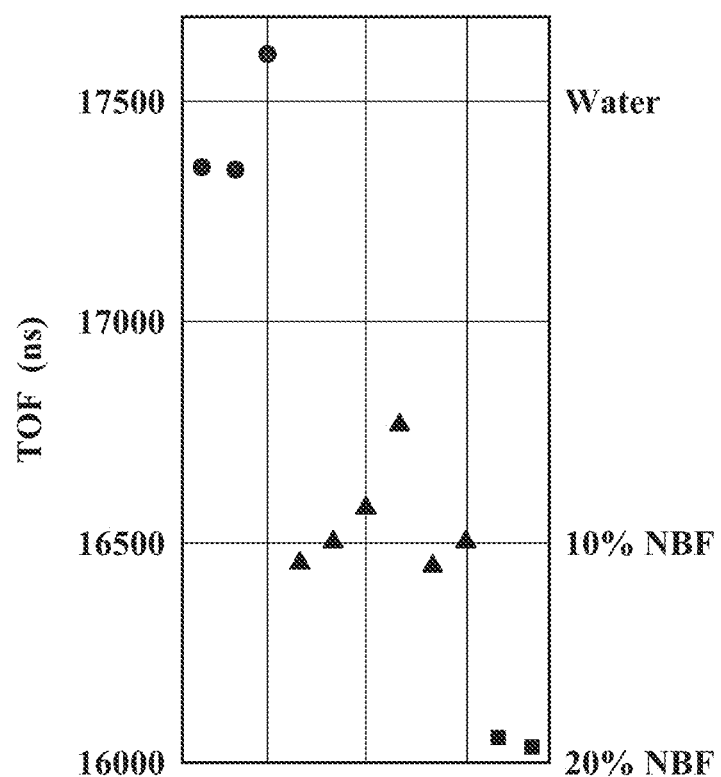
FIG. 43 is a plot of time of flight for water, 10% NBF, and 20% NBF.

FIG. 43 shows TOF of different liquids at the same temperature. Because speed of sound through a liquid is dependent on the liquid's bulk modulus. TOF measurements can be used to determine the composition of liquids at a known temperature. Additionally, liquid's TOF can be measured to predict diffusion rates through a solid tissue sample. As shown in FIG. 43, the TOF for 10% NBF can be about 2.1% to about 4.4% greater than the TOF signal of 20% NBF. The TOF of water can be greater than about 3.2% to about 8% than the TOF of 10% NBF. Based on a known distance of travel by the acoustic waves, the type of fluid can be determined based on, for example, a TOF changes, temperature measurements, or the like. A diffusion algorithm can use a fluid's bulk modulus, acoustic characteristics, or other properties to determine the diffusion state in the tissue sample.

Figure 44:
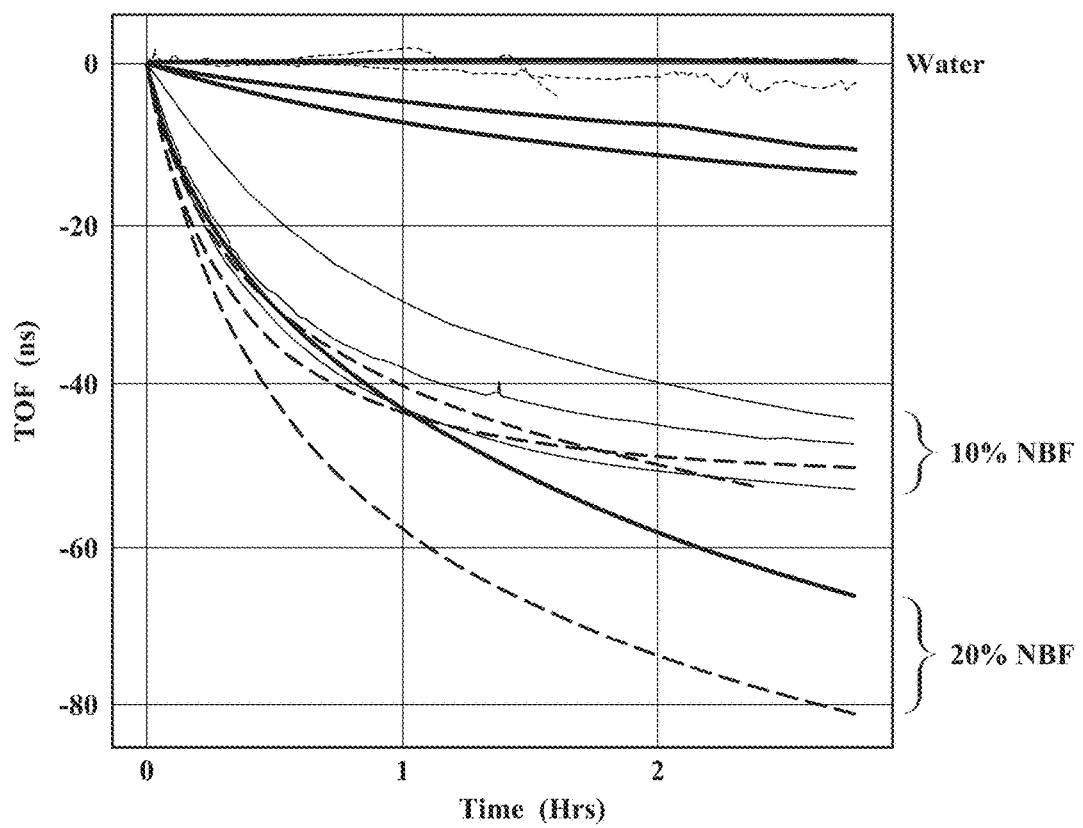
FIG. 44 is a plot of time versus time of flight for tissue samples submerged in water, 10% NBF, and 20% NBF.

FIG. 44 is a plot of time versus a change in TOF for tissue samples (cores of human tonsil with approximately 6 mm diameters) immersed in ice water (about 1° C. to about 4° C.) and different fixatives. The TOF can decrease when tissue is placed in the ice water, from about zero nanoseconds to about −13 nanoseconds for a period of about 2.8 hours. As shown in FIG. 44, the TOF can decrease generally linearly with respect to time. The TOF can decrease non-linearly from about −44 nanoseconds to about −52.5 nanoseconds when the sample is placed in 10% NBF at 40° C. for about 2.8 hours. A desired level of diffusion (or perfusion) can correspond to a target rate of change of the TOF. For example, when the TOF rate of change reaches a target TOF rate of change, the diffusion process can be inhibited or stopped by removing the sample from the 10% NBF solution. Even though the specimen is removed from the 10% NBF solution, a small amount of 10% NBF may continue to diffuse through the tissue. For 20% NBF, the TOF can decrease to about −66 nanoseconds to about −82 nanoseconds for a processing period of about 2.8 hours.

Processing systems and analyzers disclosed herein can be used to monitor movement of fluids through solid tissue samples in real-time. For example, the processing system 100 discussed in connection with FIGS. 1 and 2 can be used to monitor diffusion of media 170 through the specimen 150. If the media 170 is a fixative, it can be at a relatively low temperature to inhibit or minimize cross-linking such that changes in TOF signals primarily indicate media 170 displacing interstitial fluid rather than changes in TOF associated with cross-linking.

The computing device 160 of FIG. 1 can contain instructions for TOF acquisition schemes that determine center frequencies for TOF measurements. The scheme can include performing an initial center frequency scan to analyze phase relationships between transmitted and received ultrasound wave packets. This analyzing process can be performed to determine an optimal center frequency at which the phase difference observed by the system 100 is in a general midpoint of its comparison range. The new center frequency scheme can be a baseline and utilized as a single frequency scheme. This allows for rapid TOF acquisitions by producing an average of 100 to 1,000 phase comparisons at a rate of about 60 to 80 times per second. In some methods, the comparisons can be formed at a rate of about 70 times per second for real-time monitoring. Accordingly, the system 100 can allow monitoring of target changes up to about 120 nanoseconds at 4 MHz based on a range of phase comparator circuitry. Additionally, the center frequency can be adjusted to compensate for significant changes in TOF attributable to, for example, temperature changes, such as ambient temperature changes. The center frequency can be used to select a new midrange setting, if needed or desired. Based on the selected center frequency, the TOF can be monitored. The computing device 160 can include other TOF sampling schemes.

Referring to again to FIG. 19, the system 560 of can monitor diffusion based on TOF. The container 592a can hold fixative at a temperature less than about 15° C. In one procedure, the fixative can be within a temperature range of about −20° C. to at least 15° C., preferably greater than 0° C. to an upper temperature more typically about 10° C., and even more typically from about 3° C. to 5° C. to prevent cross-linking to a significant extent. The tissue sample can remain in contact where the fixative composition for about 15 minutes to about 4 hours. In some procedures, the contact time is about 15 minutes to 3 hours. Other times can also be used, if needed or desired. In some embodiments, the tissue samples with thicknesses of about 4 mm can be processed at fixative temperatures at about room temperature in the same container, and monitored for diffusion and cross-linking for a period of about 4 hours to about 24 hours. Thicker tissue samples (e.g., samples from resected materials) may need additional time for diffusion and cross-linking. For example, such tissue samples may be diffused up to many days using a room temperature fixative. These diffusion processes can also be monitored.

After the desired diffusion level is achieved, the transport apparatus 586 can move the tissue samples to the container 592b. The container 592b can contain a warm fixative. In some embodiments, the fixative in the container 592a is substantially the same as the fixative in container 592b. In other embodiments, concentrations and/or temperatures of fixatives in the container 592a, 592b can be different. The temperature of the fixative in container 592b can be in a range of about 22° C. to about 50° C. After a desired level of fixation is achieved, tissue samples can be moved from container 592b.

Figure 45:
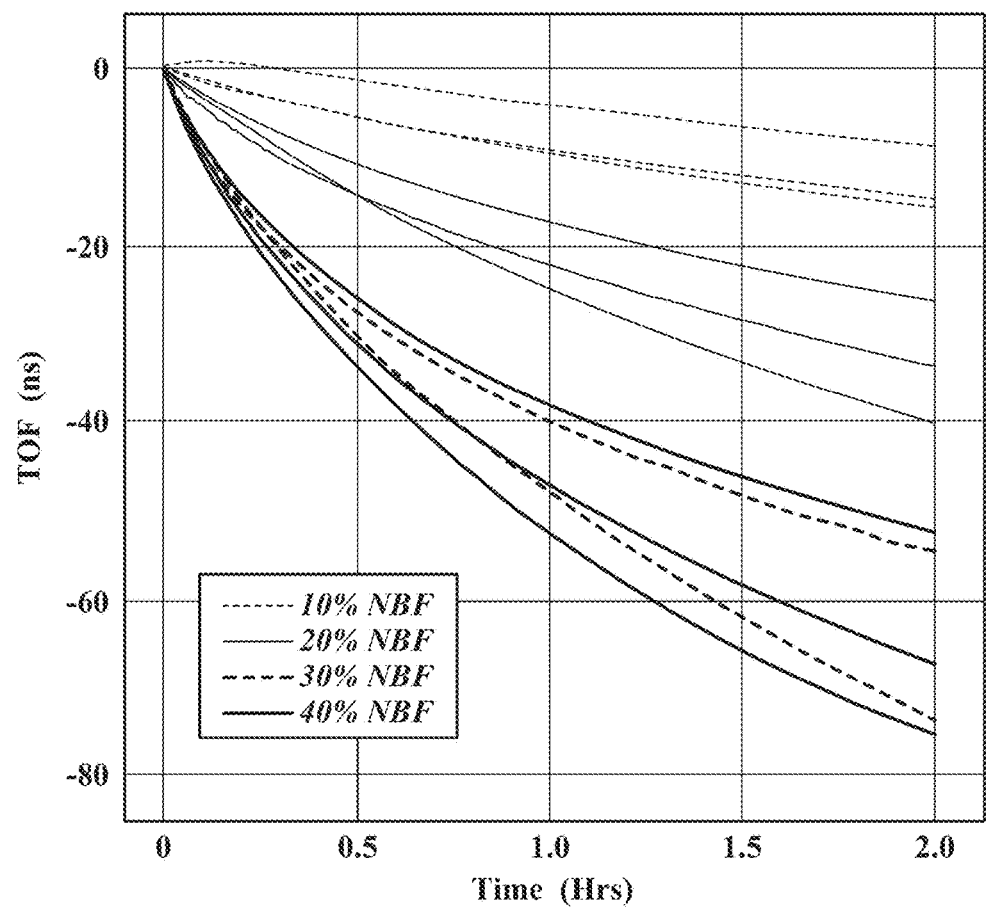
FIG. 45 is a plot of time versus time of flight for tissue samples during cold diffusion.

FIG. 45 is a plot of time versus a change in TOF for tissue samples pre-soaking in 10% NBF, 20% NBF, 30% NBF, and 40% NBF. The higher concentration fixatives (e.g., 40% NBF) provide large TOF changes that can be accurately monitored to determine the status of tissue samples. Based on the composition of the fixative and measured TOF, the diffusion time can be approximated to ensure that the diffusion process is completed.

It should be noted that, as used in this specification and the appended claims, the singular forms "a," "an," and "the" include plural referents unless the content clearly dictates otherwise. Thus, for example, reference to an analyzer including "a transmitter" includes a single transmitter, or two or more transmitters. It should also be noted that the term "or" is generally employed in its sense including "and/or" unless the content clearly dictates otherwise.

The various embodiments and features described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for preparing a tissue sample having a thickness of not more than 5 mm, comprising:
   immersing a tissue sample, which is in an unfixed state, in a fixative having a temperature ranging from between about −15° C. to about 15° C.;
   monitoring diffusion of the fixative across a thickness of the tissue sample by continuously monitoring a rate of change in time of flight of acoustic waves that travel through the tissue sample, wherein the rate of change in time of flight (TOF) is calculated by a system comprising a computing device communicatively coupled to a transmitter and a receiver, wherein:
   said transmitter outputs acoustic waves that pass through the tissue sample,
   said receiver receives the acoustic waves that have passed through the tissue sample and sends signals to the computing device in response to the received energy, and
   the computing device analyzes signals from the receiver to calculate the TOF;

continuing diffusion at least until a target rate of change of TOF is achieved; and increasing the temperature of the fixative in which the tissue sample is immersed to a temperature in a range from about 22° C. to about 50° C. after the fixative has diffused across most of a thickness of a tissue sample.

2. The method of claim 1, wherein the fixative comprises liquid formalin.

3. The method of claim 1, wherein monitoring the diffusion of the fixative includes detecting displacement of interstitial fluid in the tissue sample by acoustically evaluating the tissue sample while the fixative moves through the tissue sample.

4. The method of claim 1, wherein monitoring the diffusion of the fixative comprises simultaneously measuring diffusion of the fixative and cross-linking performed at the same temperature.

5. The method of claim 1, wherein monitoring the diffusion includes measuring time of flight of the acoustic waves at least 50 times per second.

6. The method of claim 1, wherein time of flight (TOF) is determined according to Formula I:

$$TOF = t1 + t2 + t3 \quad (I)$$

wherein:
- $t1$ is an individual travel time of the acoustic waves traveling from the transmitter to the tissue sample,
- $t2$ is the individual travel time of the acoustic waves traveling through the tissue sample, and
- $t3$ is an individual travel time of the acoustic waves traveling from tissue sample to receiver.

7. The method of claim 1, further comprising measurement of a reference TOF and compensation of the TOF measurements of the tissue sample based on the reference TOF.

8. The method of claim 1, wherein the system allows monitoring of target changes up to about 120 nanoseconds at 4 MHz.

9. The method of claim 1, wherein the tissue sample is immersed in a cold fixative at a temperature of from 0 ° C. to 10 ° C.

10. A method for preparing a fixed tissue sample having a thickness of not more than 5 mm, comprising:

immersing a tissue sample, which is in an unfixed state, in a cold fixative wherein the cold fixative is at a temperature ranging from between about 0° C. to about 10° C.;

monitoring a rate of change in time of flight of acoustic waves that travel through the tissue sample, wherein the rate of change in time of flight (TOF) is calculated by a system comprising a computing device communicatively coupled to a transmitter and a receiver, wherein the transmitter outputs acoustic waves that pass through the tissue sample, the receiver receives the acoustic waves that have passed through the tissue sample and sends signals to the computing device in response to the received energy, and the computing device analyzes signals from the receiver to calculate the TOF;

continuing diffusion of the cold fixative at least until a target rate of change of TOF is achieved; and after the target rate of change of TOF is achieved, heating the tissue sample to promote cross-linking of the tissue sample at a temperature ranging from between about 22° C. to about 50° C., wherein the target rate of change is a rate of change indicative that the cold fixative has diffused across most of a thickness of the tissue sample.

11. The method of claim 10, further comprising embedding said tissue sample in paraffin after completion of the fixation process.

12. The method of claim 11, further comprising sectioning said embedded tissue.

13. The method of claim 1, wherein the computing device is configured in a transmission mode.

14. The method of claim 13, wherein the computing device is configured in a shadowed transmission mode.

15. The method of claim 13, wherein the computing system calculates a reference TOF measurement of the fixative and compensates the TOF measured through the sample based on the reference TOF measurement.

16. The method of claim 10, wherein the fixative comprises liquid formalin.

17. The method of claim 10, wherein monitoring the diffusion of the fixative includes detecting displacement of interstitial fluid in the tissue sample by acoustically evaluating the tissue sample while the fixative moves through the tissue sample.

18. The method of claim 10, wherein monitoring the diffusion of the fixative comprises simultaneously measuring diffusion of the fixative and cross-linking performed at the same temperature.

* * * * *